(12) United States Patent
Dixon et al.

(10) Patent No.: US 9,687,832 B2
(45) Date of Patent: Jun. 27, 2017

(54) BIFUNCTIONAL ORGANIC CATALYSTS

(71) Applicant: Isis Innovation Limited, Oxford, Oxfordshire (GB)

(72) Inventors: Darren J. Dixon, Oxford (GB); Alistair J. Farley, Oxford (GB); Marta G. Núñez, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 14/438,543

(22) PCT Filed: Oct. 28, 2013

(86) PCT No.: PCT/GB2013/052808
§ 371 (c)(1),
(2) Date: Apr. 24, 2015

(87) PCT Pub. No.: WO2014/064466
PCT Pub. Date: May 1, 2014

(65) Prior Publication Data
US 2015/0298109 A1    Oct. 22, 2015

(30) Foreign Application Priority Data

Oct. 26, 2012 (GB) .................................. 1219300.9

(51) Int. Cl.
| | | |
|---|---|---|
| *B01J 31/02* | (2006.01) | |
| *C07C 335/20* | (2006.01) | |
| *C07D 207/16* | (2006.01) | |
| *C07F 9/50* | (2006.01) | |
| *C07F 9/53* | (2006.01) | |
| *C07F 9/58* | (2006.01) | |
| *C07F 9/655* | (2006.01) | |
| *C07F 9/535* | (2006.01) | |
| *C07F 9/6553* | (2006.01) | |

(52) U.S. Cl.
CPC ....... *B01J 31/0271* (2013.01); *B01J 31/0218* (2013.01); *B01J 31/0232* (2013.01); *B01J 31/0241* (2013.01); *B01J 31/0249* (2013.01); *B01J 31/0267* (2013.01); *C07C 335/20* (2013.01); *C07D 207/16* (2013.01); *C07F 9/5054* (2013.01); *C07F 9/5355* (2013.01); *C07F 9/588* (2013.01); *C07F 9/65515* (2013.01); *C07F 9/655345* (2013.01); *B01J 2231/346* (2013.01)

(58) Field of Classification Search
CPC .............. B01J 31/0241; B01J 2231/346; B01J 31/0218; B01J 31/0232; B01J 31/0249; B01J 31/0267; B01J 31/0271; C07C 335/20; C07D 207/16; C07F 9/5054; C07F 9/5355; C07F 9/588; C07F 9/65515; C07F 9/655345

USPC .......... 546/22; 548/531; 549/218, 6; 564/12, 564/27
See application file for complete search history.

(56) References Cited

U.S. PATENT DOCUMENTS 5,539,082 A * 7/1996 Nielsen .................... B82Y 5/00
                                                    530/300
2015/0336915 A1* 11/2015 Engelking ............ C07D 225/02
                                                    540/454

FOREIGN PATENT DOCUMENTS

GB              1430074 A       3/1976

OTHER PUBLICATIONS

Gololobov ("Reactions of trivalent phosphorus compounds with azides containing a mobile H-atom. A conception of phosphazo-compound spirocyclization mechanism" Tetrahedron, vol. 41, No. 4, p. 793-9, 1985.*
Golding "Convenient Routes to Alkyl-Substituted Polyamines" Tetrahedron Letters, vol. 29, No. 50, p. 6651-6654, 1988.*
Knapp "Amino Protection Using Triazones" Tetrahedron Letters, vol. 31, No. 15, p. 2109-2112, 1990.*
Chemical Abstracts Service, Database accession No. 1989:75405, Dec. 31, 1988, 2 pages.
Wanner, M., et al., New Phosphonium Ylides by Functionalization of Triphenylphosphoranylideneacetamide, Tetrahedron Letters, Dec. 31, 1992, vol. 33, No. 11, pp. 1513-1516.
Chemical Abstracts Service, Database accession No. 2011:726830, Dec. 31, 2011, 2 pages.
Chemical Abstracts Service, Database accession No. 1986:5923, Dec. 31, 1985, 3 pages.
Chemical Abstracts Service, Database accession No. 1995:435691, Apr. 25, 1994, 2 pages.
Barber, D.M., et al., One-Pot Catalytic Enantioselective Synthesis of Tetrahydropyridines via a Nitro-Mannich/Hydroanimation Cascade, Organic Letters, Oct. 19, 2012, vol. 14, No. 20, pp. 5290-5293.

(Continued)

*Primary Examiner* — Jafar Parsa
*Assistant Examiner* — Amy C Bonaparte
(74) *Attorney, Agent, or Firm* — Hodgson Russ LLP

(57) ABSTRACT

The present invention provides a bifunctional catalyst of the formula (1): wherein: each $R^1$ is independently selected from an optionally substituted alkyl group, an optionally substituted cycloalkyl group, an optionally substituted aryl group, an optionally substituted heteroaryl group, an optionally substituted aralkyl group and an optionally substituted alkaryl group; Z represents a divalent organic linking moiety optionally containing one or more stereocenters; and EWG represents an electron-withdrawing group.

$$(R^1)_3P=N—Z—NH-EWG \qquad (1)$$

10 Claims, No Drawings

(56) References Cited

OTHER PUBLICATIONS

Nunez, M.G., et al., Bifunctional Iminophosphorane Organocatalysts for Enantioselective Synthesis: Appliaction to the Ketimine Nitro-Mannich Reaction, Journal of the American Chemical Society, Nov. 6, 2013, vol. 135, No. 44, pp. 16348-16351.

Li et al., Highly Enantioselective Conjugate Addition of Malonate and b-Ketoester to Nitro alkenes: Asymmetric C—C Bond Formation with New Bifunctional Organic Catalysts Based on Cinchona Alkaloids, J. of the American Chemical Society, 2004, vol. 126, pp. 9906-9907.

Marcelli et al., Asymmetric Organocatalytic Henry Reaction, Angewandte Chemie International Edition, 2006, vol. 45, pp. 929-931.

McCooey & Connon, Urea- and Thiourea-Subs. Cinchona Alkaloid Derivatives as Highly Efficient Bifunctional Organocatalysts for the Asymmetric Addition of Malonate to Nitroalkenes: Inversion of Configuration at C9 Dramatically Improves Catalyst Performance, Angewandte Chemie International Edition, 2005, vol. 44, pp. 6367-6370.

Ye et al., Enantioselective organocatalytic Michael addition of malonate esters to nitro olefins using bifunctional cinchonine derivatives, Chemical Communications, 2005, pp. 4481-4483.

Vakulya et al., Highly Enantioselective Conjugate Addition of Nitromethane to Chalcones Using Bifunctional Cinchona Organocatalysts, Organic Letters, 2005, vol. 7, No. 20, pp. 1967-1969.

Li et al., Asymmetric Michael Addition of Arylthiols to a,b-Unsaturated Carbonyl Compounds Catalyzed by Bifunctional Organocatalysts, Synlett, 2005, No. 4, pp. 603-606.

Okino et al., Enantioselective Michael Reaction of Malonates to Nitroolefins Catalyzed by Bifunctional Organocatalysts, J. of the American Chemical Society, 2003, vol. 125, pp. 12672-12673.

Berkessel et al., Second-generation organocatalysts for the highly enantioselective dynamic kinetic resolution of azlactones, Chemical Communications, 2005, pp. 1898-1900.

Probst et al., Cooperative Assistance in Bifunctional Organocatalysis: Enantioselective Mannich Reactions with Aliphatic and Aromatic Imines, Angewandte Chemie International Edition, 2012, vol. 51, pp. 8495-8499.

\* cited by examiner

BIFUNCTIONAL ORGANIC CATALYSTS

The work leading to this invention has received funding from the European Union Seventh Framework Programme (FP7/2007 to 2013) under grant agreement no. 254637.

This present invention relates to bifunctional organocatalysts containing a basic functional group and a hydrogen bond donor. In particular, the invention relates to bifunctional organocatalysts comprising a basic iminophosphorane group and a hydrogen bond donor group. The invention also provides chemical reactions catalysed by the bifunctional organocatalysts of the invention. Also provided are synthetic precursors of the bifunctional organocatalysts and methods of synthesising the bifunctional organocatalysts.

The use of organic molecules to catalyse chemical transformations is well-known in the art. Nucleophilic catalysts such as 4-dimethylaminopyridine (DMAP), 1,4-diazabicyclo[2.2.2]octane (DABCO) and quinuclidine are widely used as catalysts for the formation of esters and for Baylis-Hillman reactions. Proline and derivatives thereof have been used as chiral catalysts, notably for asymmetric aldol reactions, although high catalyst loadings are often required.

In recent years, a number of bifunctional organocatalysts have been reported. In particular, a number of organocatalysts are known which contain both basic and hydrogen bond donor functionality. These combine the capacity to activate and organise electrophilic substrates via hydrogen bonding with the activation of pro-nucleophilic reagents via deprotonation. Where the bifunctional catalysts are chiral, catalysed reactions may proceed with high levels of stereocontrol.

Among the most successful bifunctional organocatalysts of this type are those derived from cinchona alkaloids, such as I (Deng et al., Journal of the American Chemical Society 2004, volume 126, pages 9906-9907), II (Hiemstra et al., Angewandte Chemie International Edition, 2006, volume 45, pages 929-931) and III (Connon et al., Angewandte Chemie International Edition 2005, volume 44, pages 6367-6370; Dixon et al., Chemical Communications, 2005, pages 4481-4483; Sóos et al., Organic Letters, 2005, volume 7, pages 1967-1969; Chen et al., Synlett, 2005, pages 603-606), and the cyclohexane-1,2-diamine derivatives IV (Takemoto et al., Journal of the American Chemical Society 2003, volume 125, pages 12672-12673) and V (Berkessel et al., Chemical Communications, 2005, pages 1898-1900). However, despite the surge of interest in this field in the last decade, reaction rates are often low, high catalyst loadings are often required, and the range of compatible pro-nucleophiles and electrophilic substrates is limited.

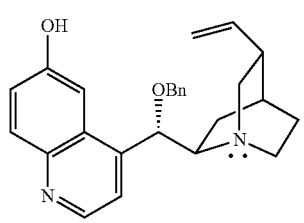

I

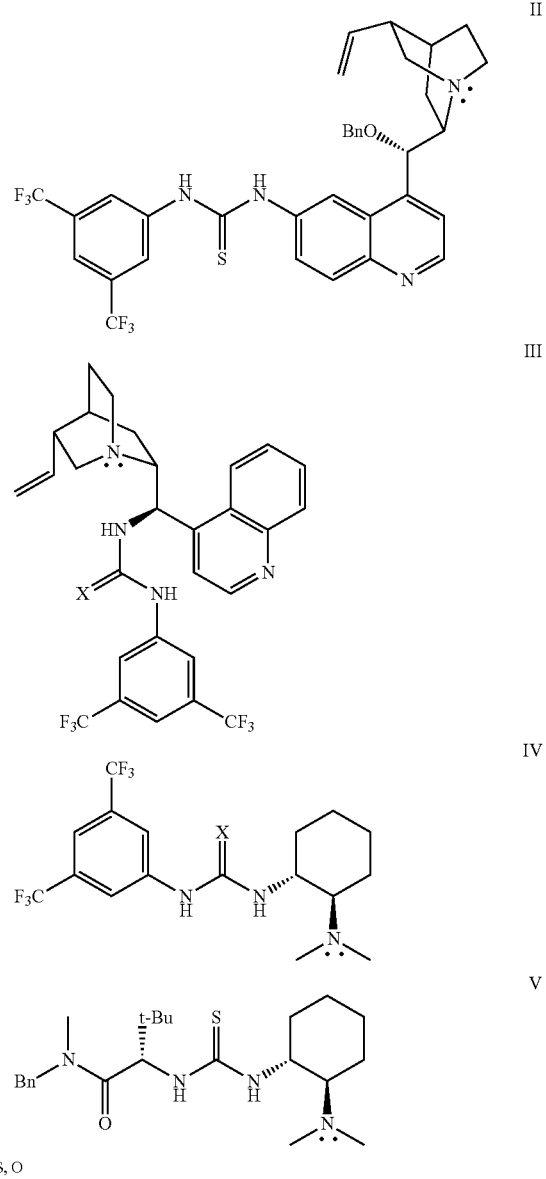

X = S, O

Accordingly, there remains a need in the art for new bifunctional organocatalysts which provide enhanced reactivity compared to those currently available in the art. In particular, there is a need in the art for new chiral bifunctional organocatalysts which provide both enhanced activity and high levels of stereocontrol. Preferably, such enhanced reactivity would be obtainable even with low catalyst loadings. In addition, such bifunctional organocatalysts would preferably be amenable to library generation so as to facilitate optimisation procedures.

The present invention is based at least in part on a realisation that an inherent restriction of existing bifunctional organocatalysts is the fixed nature of the basic functionality. The present inventors have recognised that low-acidity pro-nucleophiles and/or low energy electrophiles often do not react at all in the presence of existing bifunctional organocatalysts owing to negligible activation of the pro-nucleophile by the weak basic functionality. Furthermore, adaptation of existing systems to address this defect is not readily achievable. Cinchona alkaloids-derived catalysts such as I, II and III, are dependent on the availability of precursors from the chiral pool and no modification of the basic bridgehead nitrogen atom is possible. In systems such as IV and V, the size of the tertiary amine group may be varied by changing the alkyl substituents on the nitrogen atom. However, this has minimum effect on the basicity of this group. Furthermore, in these systems, the incorporation of the N,N-dialkylamine groups occurs early in the synthesis, thereby making library generation laborious since there is no late-stage branch point in the synthesis to install alternative tertiary amines. Accordingly, the present invention provides new bifunctional organocatalysts which aim to address one or more of these deficiencies of existing systems.

In a first aspect, the present invention provides a catalyst having the formula (1):

$(R^1)_3P{=}N{-}Z{-}NH\text{-}EWG$ (1)

wherein:
each $R^1$ is independently selected from an optionally substituted alkyl group, an optionally substituted cycloalkyl group, an optionally substituted aryl group, an optionally substituted heteroaryl group, an optionally substituted aralkyl group and an optionally substituted alkaryl group;
Z represents a divalent organic linking moiety optionally containing one or more stereocentres; and
EWG represents an electron-withdrawing group.

It has surprisingly been found that compounds having the formula (1) are effective bifunctional catalysts which overcome many of the limitations of existing bifunctional organocatalyst systems. The iminophosphorane group $[(R^1)_3P{=}N\text{-}]$ is Brønsted basic and its basicity is readily variable/tunable by modification of the groups $R^1$. By linking the basic iminophosphorane group to a variable/tunable hydrogen bond donor, the bifunctional organocatalysts of the invention may provide increased activity and broader applicability than the bifunctional organocatalysts previously reported. Furthermore, the use of a variable/tunable linking moiety Z containing one or more stereocentres, provides a new route to stereocontrolled reactions.

Catalysts of formula (1) containing a range of different iminophosphorane groups and hydrogen bond donor groups can readily be synthesised from widely available precursors. In particular, suitable chiral linking groups (Z) are readily obtainable from the chiral pool and commercially available. The iminophosphorane group is readily prepared by the Staudinger reaction of a phosphine of the formula $(R^1)_3P$ with an azide precursor. This reaction may proceed smoothly under mild conditions to give iminophosphoranes in high yield and without noticeable formation of any by-products other than the dinitrogen that is eliminated. Since many phosphine reagents are commercially available or readily synthesised, their combination with varied organoazides linked to hydrogen bond donors gives access to a large number of different catalysts. The bifunctional organocatalysts of the invention are therefore readily amenable to library generation via combinatorial methods, facilitating the rapid identification of optimum catalyst structures in any reaction of interest.

For the purposes of the present invention, the following terms as used herein shall, unless otherwise indicated, be understood to have the following meanings.

The term "hydrocarbyl" as used herein refers to a group consisting exclusively of hydrogen and carbon atoms, the group having from 1 to 30 carbon atoms. For instance, a hydrocarbyl group may have from 1 to 20 carbon atoms, e.g. from 1 to 12 carbon atoms, e.g. from 1 to 10 carbon atoms. A hydrocarbyl group may be an acyclic group, a cyclic group, or may comprise both an acyclic portion and a cyclic portion. Unless stated otherwise, the term "hydrocarbyl" refers to a monovalent group. Examples of hydrocarbyl groups include alkyl, alkenyl, alkynyl, carbocyclyl (e.g. cycloalkyl, cycloalkenyl or aryl) and aralkyl.

The term "alkyl" as used herein refers to a straight or branched chain alkyl moiety having from 1 to 30 carbon atoms. For instance, an alkyl group may have from 1 to 20 carbon atoms, e.g. from 1 to 12 carbon atoms, e.g. from 1 to 10 carbon atoms. In particular, an alkyl group may have 1, 2, 3, 4, 5 or 6 carbon atoms. Examples of alkyl groups include methyl, ethyl, propyl (n-propyl or isopropyl), butyl (n-butyl, sec-butyl or tert-butyl), pentyl, hexyl and the like.

The term "alkenyl" as used herein refers to a straight or branched chain alkyl group having from 2 to 30 carbon atoms and having, in addition, at least one carbon-carbon double bond, of either E or Z stereochemistry where applicable. For instance, an alkenyl group may have from 2 to 20 carbon atoms, e.g. from 2 to 12 carbon atoms, e.g. from 2 to 10 carbon atoms. In particular, an alkenyl group may have 2, 3, 4, 5 or 6 carbon atoms. Examples of alkenyl groups include ethenyl, 2-propenyl, 1-butenyl, 2-butenyl, 3-butenyl, 1-pentenyl, 2-pentenyl, 3-pentenyl, 1-hexenyl, 2-hexenyl, 3-hexenyl and the like.

The term "alkylene" refers to a divalent straight or branched chain saturated hydrocarbyl group having from 1 to 30 carbon atoms. For instance, an alkylene group may have from 1 to 20 carbon atoms, e.g. from 1 to 12 carbon atoms, e.g. from 1 to 10 carbon atoms. In particular, an alkylene group may have 1, 2, 3, 4, 5 or 6 carbon atoms.

The term "alkoxy" as used herein refers to —O-alkyl, wherein alkyl is as defined above. In some instances, an alkoxy group may have from 1 to 20 carbon atoms, e.g. from 1 to 12 carbon atoms, e.g. from 1 to 10 carbon atoms. In particular, an alkoxy group may have 1, 2, 3, 4, 5 or 6 carbon atoms. Examples of alkoxy groups include methoxy, ethoxy, propoxy, isopropoxy, butoxy, tert-butoxy, pentoxy, hexoxy and the like.

The term "cycloalkyl" as used herein refers to a saturated aliphatic hydrocarbyl moiety having from 3 to 20 carbon atoms and containing at least one ring, wherein said ring has at least 3 ring carbon atoms. For instance, a cycloalkyl group may have from 3 to 16 carbon atoms, e.g. from 3 to 10 carbon atoms. In particular, a cycloalkyl group may have 3, 4, 5 or 6 ring carbon atoms. A cycloalkyl group may be a monocyclic, polycyclic (e.g. bicyclic) or bridged ring system. Examples of cycloalkyl groups include cyclopropyl, cyclobutyl, cyclopentyl, cyclohexyl, norbornyl, adamantyl and the like.

The term "aryl" as used herein refers to an aromatic carbocyclic ring system having from 6 to 30 ring carbon atoms. For instance, an aryl group may have from 3 to 16 ring carbon atoms, e.g. from 3 to 10 ring carbon atoms. An aryl group may be a monocyclic aromatic ring system or a polycyclic ring system having two or more rings, at least one of which is aromatic. Examples of aryl groups include phenyl, naphthyl, fluorenyl, azulenyl, indenyl, anthryl and the like.

The term "aryloxy" as used herein refers to —O-aryl, wherein aryl is as defined above. In some instances, an aryloxy group may have from 6 to 20 carbon atoms, e.g. from 6 to 14 carbon atoms, e.g. from 6 to 10 carbon atoms. Examples of aryloxy groups include phenoxy and the like.

The term "aralkyl" as used herein refers to an alkyl group substituted with an aryl group, wherein the alkyl and aryl groups are as defined herein. In one embodiment, an alkyl group may be substituted with one aryl group. In another embodiment, an alkyl group may be substituted with two or more aryl groups. An example of an aralkyl group is benzyl.

The term "alkaryl" as used herein refers to an aryl group substituted with one or more alkyl groups, wherein the alkyl and aryl groups are as defined herein. An example of an alkaryl group is tolyl.

The term "heterocyclyl" as used herein refers to a saturated (e.g. heterocycloalkyl) or unsaturated (e.g. heteroaryl) heterocyclic ring moiety having from 3 to 30 ring atoms, wherein said ring atoms include at least one ring carbon atom and at least one ring heteroatom selected from nitrogen, oxygen, phosphorus, silicon and sulphur. For instance, a heterocyclyl group may have from 3 to 20 ring atoms, e.g. from 3 to 16 ring atoms, e.g. from 3 to 10 ring atoms. In particular, a heterocyclyl group may have 5 or 6 ring atoms, and may be saturated or unsaturated.

The term "heteroaryl" as used herein refers to an aromatic heterocyclic ring system having from 5 to 16 ring atoms, wherein said ring atoms include at least one ring carbon atoms and at least one ring heteroatom selected from nitrogen, oxygen and sulphur. The group may be a monocyclic ring system or a polycyclic (e.g. bicyclic) ring system, having two or more rings, at least one of which is aromatic. Examples of heteroaryl groups include pyridazinyl, pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl and the like.

The term "optionally substituted" as used herein means unsubstituted or substituted.

The term "substituted" as used herein as used in connection with a chemical group means that one or more (e.g. 1, 2, 3, 4 or 5) of the hydrogen atoms in that group are replaced independently of each other by a corresponding number of substituents. It will, of course, be understood that the one or more substituents may only be at positions where they are chemically possible, i.e. that any substitution is in accordance with permitted valence of the substituted atom and the substituent and that the substitution results in a stable compound. The term is contemplated to include all permissible substituents of a chemical group or compound. It will be understood by those skilled in the art that one or more hydrogen atoms on a given substituent can themselves be substituted, if appropriate.

Where two or more moieties are described as being "each independently" selected from a list of moieties, this means that the moieties may be the same or different. The identity of each moiety is therefore independent of the identities of the one or more other moieties. Where multiple substituents are indicated as being attached to a structure, it will be understood that the substituents can be the same or different.

The term "electron withdrawing group" as used herein refers to any atom or group having electronegativity greater than that of a hydrogen atom, wherein electronegativity is as defined on the Pauling scale. A quantification of the level of electron withdrawing capability is given by the Hammett sigma ($\sigma$) constant. This constant is well known in the art (see e.g. "Advanced Organic Chemistry", J. March, McGraw Hill, New York, 2007). The Hammett sigma constant values are generally positive for electron withdrawing groups.

The term "$\pi$-bond" as used herein refers to a chemical bond formed by the overlap of p orbitals on adjacent atoms, perpendicular to any sigma ($\sigma$) bonds between the same atoms. A $\pi$-bond is generally a double or triple bond. Examples of $\pi$-bonds include C=C, C≡C, C=O, C=N, C≡N, N=O and S=O bonds.

Each $R^1$ is preferably independently selected from an optionally substituted ($C_1$-$C_{10}$)alkyl group, an optionally substituted ($C_3$-$C_{10}$)cycloalkyl group, an optionally substituted ($C_6$-$C_{10}$)aryl group, an optionally substituted ($C_4$-$C_9$) heteroaryl group, an optionally substituted ($C_7$-$C_{14}$)aralkyl group and an optionally substituted ($C_7$-$C_{14}$)alkaryl group.

More preferably, each $R^1$ is independently an optionally substituted ($C_1$-$C_{10}$)alkyl group, an optionally substituted ($C_3$-$C_{10}$)cycloalkyl group, an optionally substituted ($C_6$-$C_{10}$)aryl group, an optionally substituted ($C_7$-$C_{14}$)aralkyl group or an optionally substituted ($C_7$-$C_{14}$)alkaryl group. More preferably, each $R^1$ is independently an optionally substituted ($C_1$-$C_{10}$)alkyl group, an optionally substituted ($C_3$-$C_{10}$)cycloalkyl group or an optionally substituted ($C_6$-$C_{10}$)aryl group. Still more preferably, each $R^1$ is independently an optionally substituted ($C_1$-$C_{10}$)alkyl group or an optionally substituted ($C_6$-$C_{10}$)aryl group. Most preferably, each $R^1$ is independently an optionally substituted phenyl group.

Where $R^1$ is substituted, preferred substituents include ($C_1$-$C_4$)alkoxy, —F, —Cl, —Br, —I, —$CF_3$, —$C_2F_5$ and —$NO_2$. In particular, where $R^1$ is an aryl or heteroaryl group, substitution of the aromatic ring by one or more activating substituents, such as alkoxy groups, is preferred.

More preferably, each $R^1$ is independently selected from methyl, ethyl, n-propyl, iso-propyl, n-butyl, iso-butyl, sec-butyl, tert-butyl, cyclopropyl, cyclobutyl, cyclopentyl, cyclohexyl, cycloheptyl, adamantyl, phenyl, 4-methoxyphenyl, 3,4-dimethoxyphenyl, 3,4,5-trimethoxyphenyl, 4-methylphenyl, 3,4-dimethylphenyl, 3,4,5-trimethylphenyl and naphthyl. In some embodiments, each $R^1$ is independently an aryl or alkaryl group selected from phenyl, 4-methoxyphenyl, 3,4-dimethoxyphenyl, 3,4,5-trimethoxyphenyl, 4-methylphenyl, 3,4-dimethylphenyl, 3,4,5-trimethylphenyl and naphthyl. In further embodiments, each $R^1$ is independently an alkyl group selected from methyl, ethyl, n-propyl, iso-propyl and n-butyl. In particularly preferred embodiments, each $R^1$ is independently selected from phenyl, 4-methoxyphenyl and n-butyl. More preferably, each $R^1$ is phenyl or 4-methoxyphenyl, and most preferably each $R^1$ is phenyl.

Preferably, each $R^1$ is the same.

The divalent organic linking moiety Z may in principle be any organic group that is effective to link the iminophosphorane group [$(R^1)_3$P=N-] to the hydrogen bond donor group [—NH-EWG] and which is compatible with the use of the compound as an organocatalyst. Suitable linking moieties can readily be identified by the skilled person and include, for example, optionally substituted hydrocarbyl moieties. Preferably, the linking moiety Z is an optionally substituted ($C_2$-$C_{10}$)alkylene group, more preferably an optionally substituted ($C_2$-$C_6$)alkylene group, such as an optionally substituted ($C_2$-$C_4$)alkylene group. However, it is not excluded that the linking moiety Z might contain, for example, one or more aromatic or heteroaromatic rings and/or one or more heteroatoms between the iminophosphorane and hydrogen bond donor groups, provided that any heteroatoms are compatible with the use of the compound as an organocatalyst.

Where the linking moiety Z contains one or more stereocentres the catalyst of formula (1) may be chiral. Chiral catalysts of formula (1) may be used as a racemate or in enantiomerically-enriched form. Preferably, chiral catalysts of formula (1) are used as single stereoisomers. In some embodiments, chiral catalysts of formula (1) may be used to provide reaction products with high levels of stereocontrol.

The term "single stereoisomer" as used herein indicates that the catalyst has an enantiomeric excess (e.e.) of at least 90%, more preferably at least 95%, still more preferably at least 98% and most preferably at least 99%. If the compound may exist as a mixture of diastereomers, then the term "single stereoisomer" as used herein further indicates that the catalyst has a diastereomeric excess (d.e.) of at least 90%, more preferably at least 95%, still more preferably at least 98% and most preferably at least 99%. The use of wedge bonds or dashed bonds to indicate stereochemistry in chemical formulae herein shall be interpreted as meaning that the compound is a single stereoisomer.

The electron withdrawing group (EWG) is preferably selected from groups having the formula —C(=X)NHR$^2$, —C(=X)R$^2$, —SO$_2$R$^2$ and —C(=X)XR$^2$, wherein X is selected from O and S, and wherein R$^2$ is selected from an optionally substituted alkyl group, an optionally substituted cycloalkyl group, an optionally substituted aryl group, an optionally substituted heteroaryl group, an optionally substituted aralkyl group and an optionally substituted alkaryl group.

More preferably, the electron withdrawing group (EWG) is selected from —C(=X)NHR$^2$, wherein X is S or O, —C(=O)R$^2$, —SO$_2$R$^2$ and —C(=O)OR$^2$. More preferably, EWG is selected from —C(=X)NHR$^2$, wherein X is S or O, and —C(=O)R$^2$. Still more preferably, EWG is selected from —C(=X)NHR$^2$, wherein X is S or O, and most preferably EWG has the formula —C(=S)NHR$^2$.

R$^2$ is preferably selected from an optionally substituted (C$_1$-C$_{10}$)alkyl group, an optionally substituted (C$_3$-C$_{10}$)cycloalkyl group, an optionally substituted (C$_6$-C$_{10}$)aryl group, an optionally substituted (C$_4$-C$_9$)heteroaryl group, an optionally substituted (C$_7$-C$_{14}$)aralkyl group and an optionally substituted (C$_7$-C$_{14}$)alkaryl group. More preferably, R$^2$ is selected from an optionally substituted (C$_1$-C$_{10}$)alkyl group, an optionally substituted (C$_3$-C$_{10}$)cycloalkyl group, an optionally substituted (C$_6$-C$_{10}$)aryl group, an optionally substituted (C$_7$-C$_{14}$)aralkyl group and an optionally substituted (C$_7$-C$_{14}$)alkaryl group. Still more preferably, R$^2$ is selected from an optionally substituted (C$_1$-C$_{10}$)alkyl group, an optionally substituted (C$_3$-C$_{10}$)cycloalkyl group and an optionally substituted (C$_6$-C$_{10}$)aryl group. Still more preferably, R$^2$ is a (C$_1$-C$_{10}$)alkyl group or an optionally substituted (C$_6$-C$_{10}$)aryl group. Most preferably, R$^2$ is an optionally substituted phenyl group.

Where R$^2$ is substituted, preferred substituents include (C$_1$-C$_4$)alkoxy, —F, —Cl, —Br, —I, —CF$_3$, —C$_2$F$_5$ and —NO$_2$. In particular, where R$^2$ is a substituted aryl or heteroaryl group, substitution of the aromatic ring by one or more electron withdrawing groups such as —CF$_3$ or —NO$_2$ may be preferred since this may increase the hydrogen bond donor strength of the hydrogen bond donor group.

R$^2$ is preferably selected from methyl, ethyl, n-propyl, iso-propyl, n-butyl, iso-butyl, sec-butyl, tert-butyl, 1,1,3,3-tetramethylbutyl, cyclopropyl, cyclobutyl, cyclopentyl, cyclohexyl, cycloheptyl, phenyl, 4-methoxyphenyl, 3,4-dimethoxyphenyl, 3,4,5-trimethoxyphenyl, 4-chlorophenyl, 4-nitrophenyl, 4-methylphenyl, 3,4-dimethylphenyl, 3,4,5-trimethylphenyl, 4-(trifluoromethyl phenyl), 3,5-bis-(trifluoromethyl)phenyl and 4-nitrophenyl.

More preferably, R$^2$ is selected from tert-butyl, phenyl, 4-methylphenyl, 4-methoxyphenyl, 4-(trifluoromethylphenyl), 3,5-bis-(trifluoromethyl)phenyl and 4-nitrophenyl. Still more preferably, R$^2$ is selected from phenyl, 4-(trifluoromethylphenyl), 3,5-bis-(trifluoromethyl)phenyl and 4-nitrophenyl. Most preferably, R$^2$ is selected from 4-(trifluoromethylphenyl), 3,5-bis-(trifluoromethyl)phenyl and 4-nitrophenyl.

In some embodiments, EWG has the following formula:

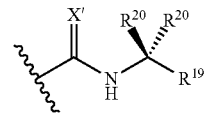

wherein:

X' is selected from S and O;

R$^{19}$ is selected from hydrogen and —C(=Z')N(R$^{21}$)$_2$, wherein Z' is selected from S and O, and each R$^{21}$ is independently selected from hydrogen, an optionally substituted (C$_1$-C$_{10}$)alkyl group, an optionally substituted (C$_3$-C$_{10}$)cycloalkyl group, an optionally substituted (C$_6$-C$_{10}$)aryl group, an optionally substituted (C$_4$-C$_9$)heteroaryl group, an optionally substituted (C$_7$-C$_{14}$)aralkyl group and an optionally substituted (C$_7$-C$_{14}$)alkaryl group; and each R$^{20}$ is independently selected from hydrogen, an optionally substituted (C$_1$-C$_{10}$)alkyl group, an optionally substituted (C$_3$-C$_{10}$)cycloalkyl group, an optionally substituted (C$_6$-C$_{10}$)aryl group, an optionally substituted (C$_4$-C$_9$)heteroaryl group, an optionally substituted (C$_7$-C$_{14}$)aralkyl group and an optionally substituted (C$_7$-C$_{14}$)alkaryl group.

Preferably X' is S.

In an embodiment, R$^{19}$ is hydrogen. In this embodiment, preferably each R$^{20}$ is not hydrogen and, more preferably, each R$^{20}$ is independently selected from an optionally substituted (C$_1$-C$_{10}$)alkyl group and an optionally substituted (C$_6$-C$_{10}$)aryl group. Preferably R$^{19}$ is hydrogen and each R$^{20}$ is different. In these instances, EWG will contain a chiral centre.

In an embodiment, R$^{19}$ is —C(=Z')N(R$^{21}$)$_2$ and preferably Z' is O and/or each R$^{21}$ is independently selected from hydrogen, an optionally substituted (C$_1$-C$_{10}$)alkyl group, an optionally substituted (C$_6$-C$_{10}$)aryl group and an optionally substituted (C$_7$-C$_{14}$)aralkyl group. In embodiments where R$^{19}$ is —C(=Z')N(R$^{21}$)$_2$, preferably one R$^{20}$ is hydrogen and the other R$^{20}$ is selected from an optionally substituted (C$_1$-C$_{10}$)alkyl group, an optionally substituted (C$_6$-C$_{10}$)aryl group, an optionally substituted (C$_7$-C$_{14}$)aralkyl group and an optionally substituted (C$_7$-C$_{14}$)alkaryl group. In these instances, EWG will contain a chiral centre.

In embodiments, EWG may contain one chiral centre or more than one chiral centre. R$^{20}$ and/or R$^{21}$ may contain one or more chiral centres.

Optional substituents for R$^{20}$ and R$^{21}$ include (C$_1$-C$_4$) alkoxy, —F, —Cl, —Br, —I, —CF$_3$, —C$_2$F$_5$ and —NO$_2$. Preferably each R$^{20}$ is unsubstituted. Preferably each R$^{21}$ is unsubstituted.

In some embodiments, EWG contains a H-bond-donor group, such as a urea or thiourea group. For example, EWG may be:

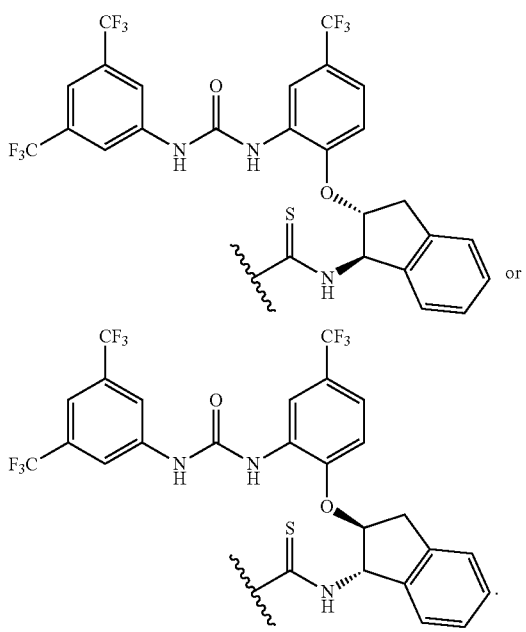

In some embodiments, the catalyst of the invention has the formula (2):

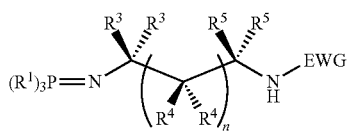

(2)

wherein:

R¹ and EWG are as defined above;

each R³, R⁴ and R⁵ is independently selected from hydrogen, an optionally substituted alkyl group, an optionally substituted cycloalkyl group, an optionally substituted aryl group, an optionally substituted heteroaryl group, an optionally substituted aralkyl group, an optionally substituted di-aryl-alkyl group and an optionally substituted alkaryl group, or any two of R³, R⁴ or R⁵ on adjacent carbon atoms may together form a methylene chain having the formula —(CH$_2$)$_m$—, wherein m is an integer of from 1 to 5; and n is an integer of from 0 to 3.

More preferably, the catalyst has the formula (3)

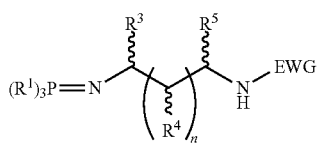

(3)

wherein:

R¹, R³, R⁴, R⁵, EWG and n are as defined above.

More preferably, the catalyst has the formula (4):

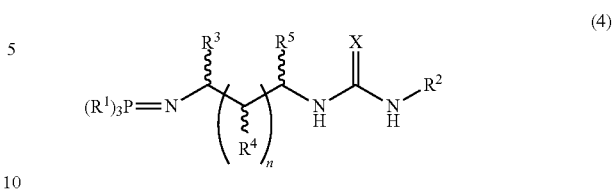

(4)

wherein:

R¹, R², R³, R⁴, R⁵, n and X are as defined above.

R³, R⁴ and R⁵ are preferably independently selected from hydrogen, an optionally substituted (C$_1$-C$_{10}$)alkyl group, an optionally substituted (C$_3$-C$_{10}$)cycloalkyl group, an optionally substituted (C$_6$-C$_{10}$)aryl group, an optionally substituted (C$_4$-C$_9$)heteroaryl group, an optionally substituted (C$_7$-C$_{14}$) aralkyl group, an optionally substituted (C$_{13}$-C$_{20}$)di-aryl-alkyl group and an optionally substituted (C$_7$-C$_{14}$)alkaryl group, or any two of R³, R⁴ or R⁵ on adjacent carbon atoms may together form a methylene chain having the formula —(CH$_2$)$_m$—, wherein m is an integer of from 3 to 5.

More preferably, R³, R⁴ and R⁵ are each independently selected from hydrogen, an optionally substituted (C$_1$-C$_{10}$) alkyl group, an optionally substituted (C$_3$-C$_{10}$)cycloalkyl group, an optionally substituted (C$_6$-C$_{10}$)aryl group, an optionally substituted (C$_7$-C$_{14}$)aralkyl group, an optionally substituted (C$_{13}$-C$_{20}$)di-aryl-alkyl group and an optionally substituted (C$_7$-C$_{14}$)alkaryl group, or any two of R³, R⁴ or R⁵ on adjacent carbon atoms may together form a methylene chain having the formula —(CH$_2$)$_m$—, wherein m is an integer of from 3 to 5. Still more preferably, R³, R⁴ and R⁵ are each independently selected from hydrogen, an optionally substituted (C$_1$-C$_{10}$)alkyl group, an optionally substituted (C$_3$-C$_{10}$)cycloalkyl group, an optionally substituted (C$_6$-C$_{10}$)aryl group and an optionally substituted (C$_7$-C$_{14}$) aralkyl group. Most preferably, R³, R⁴ and R⁵ are each independently selected from hydrogen, an optionally substituted (C$_1$-C$_{10}$)alkyl group and an optionally substituted (C$_6$-C$_{10}$)aryl group.

Where any of R³, R⁴ or R⁵ contains a substituted aryl or heteroaryl group, preferred substituents include 1 to 3 groups selected from (C$_1$-C$_4$)alkoxy, phenoxy, —F, —Cl, —Br, —I, —CF$_3$, —C$_2$F$_5$ and —NO$_2$.

R³, R⁴ and R⁵ are preferably independently selected from hydrogen, methyl, ethyl, n-propyl, iso-propyl, n-butyl, iso-butyl, sec-butyl, tert-butyl, phenyl, 4-methylphenyl, 4-methoxyphenyl, 2,5-dimethyl phenyl, benzyl, 4-methoxybenzyl, diphenylmethyl, iso-propyloxymethyl and tert-butyloxymethyl, or two of R³, R⁴ or R⁵ on adjacent carbon atoms together form a methylene chain having the formula —(CH$_2$)$_m$—, wherein m is 3 or 4.

Where R³, R⁴ or R⁵ is other than hydrogen, the adjacent carbon atom will define a chiral centre. As discussed above, chiral organocatalysts may be used as single stereoisomers in accordance with the present invention. Chiral linking groups of the formula —CHR³(CHR⁴)$_n$CHR⁵— may be derived from suitable precursors that are available from the chiral pool. Accordingly, in some embodiments of the invention, there is provided a catalyst having the formula (2) or formula (3), wherein at least one of R³, R⁴ and R⁵ is not hydrogen, more preferably wherein at least one of R³ and R⁵ is not hydrogen, and most preferably wherein R⁵ is not hydrogen.

Preferably, at least one of R³ and R⁵ is selected from methyl, ethyl, n-propyl, iso-propyl, n-butyl, iso-butyl, sec-butyl, tert-butyl, phenyl, 4-methylphenyl, 4-methoxyphenyl, 2,5-dimethyl phenyl, benzyl, 4-methoxybenzyl, diphenylmethyl, iso-propyloxymethyl and tert-butyloxymethyl, or in the case where n is 0, $R^3$ and $R^5$ together may form a methylene chain having the formula —$(CH_2)_m$—, wherein m is 3 or 4.

More preferably, at least one of $R^3$ and $R^5$ is selected from methyl, ethyl, n-propyl, iso-propyl, n-butyl, iso-butyl, sec-butyl, tert-butyl, phenyl, 4-methylphenyl, 4-methoxyphenyl, benzyl, 4-methoxybenzyl, diphenylmethyl, iso-propyloxymethyl and tert-butyloxymethyl, or in the case where n is 0, $R^3$ and $R^5$ together may form a methylene chain having the formula —$(CH_2)_m$—, wherein m is 3 or 4.

Still more preferably, $R^5$ is selected from iso-propyl, tert-butyl, phenyl, benzyl and diphenylmethyl.

Preferably, n is an integer from 0 to 2, more preferably n is 0 or 1. Most preferably n is 0.

In preferred embodiments, $R^5$ is selected from iso-propyl, tert-butyl, phenyl, benzyl and diphenylmethyl, n is 0 and $R^3$ is H.

In further preferred embodiments, n is 0 and $R^3$ and $R^5$ are both phenyl or are both benzyl or $R^3$ and $R^5$ taken together form a methylene chain of the formula —$(CH_2)_4$—.

In some embodiments, the catalyst has the formula (5) or (6):

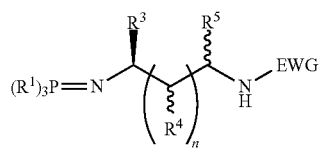

(5)

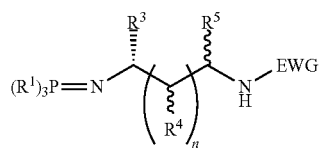

(6)

wherein: $R^1$, $R^3$, each $R^4$, $R^5$, EWG and n are as defined above, with the proviso that $R^3$ is not hydrogen; or the catalyst has the formula (7) or (8):

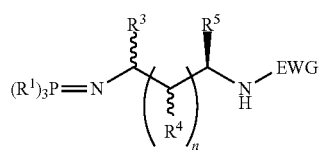

(7)

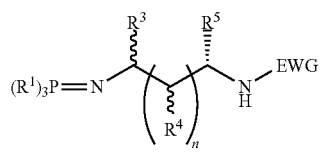

(8)

wherein: $R^1$, $R^3$, each $R^4$, $R^5$, EWG and n are as defined above, with the proviso that $R^5$ is not hydrogen.

In further embodiments, the catalyst has the formula (9) or (10):

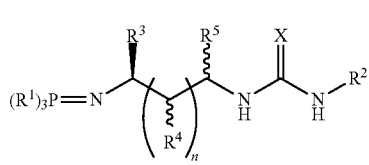

(9)

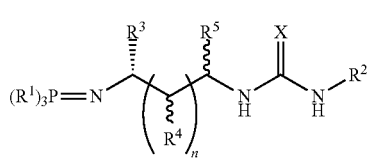

(10)

wherein: $R^1$, $R^2$, $R^3$, each $R^4$, $R^5$, X and n are as defined above, with the proviso that $R^3$ is not hydrogen; or the catalyst has the formula (11) or (12):

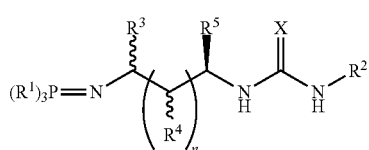

(11)

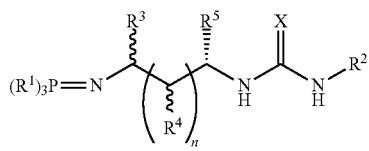

(12)

wherein: $R^1$, $R^2$, $R^3$, each $R^4$, $R^5$, X and n are as defined above, with the proviso that $R^5$ is not hydrogen.

In preferred embodiments, the catalyst has the formula (13) or (14):

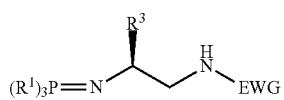

(13)

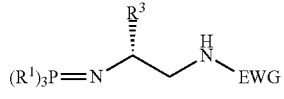

(14)

wherein: $R^1$, $R^3$, and EWG are as defined above, with the proviso that $R^3$ is not hydrogen; or the catalyst has the formula (15) or (16):

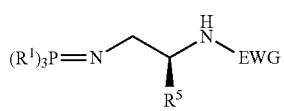

(15)

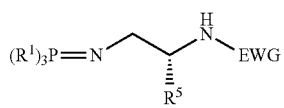

(16)

wherein: $R^1$, $R^5$, and EWG are as defined above, with the proviso that $R^5$ is not hydrogen;

or the catalyst has the formula (17), (18), (19) or (20):

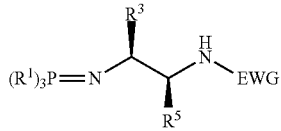
(17)

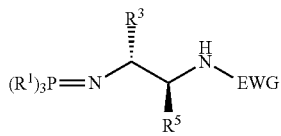
(18)

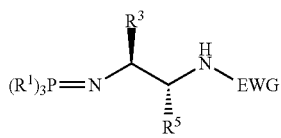
(19)

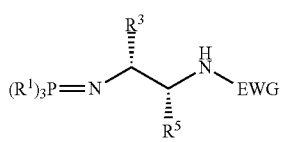
(20)

wherein: $R^1$, $R^3$, $R^5$ and EWG are as defined above, with the provisos that $R^3$ is not hydrogen and $R^5$ is not hydrogen.

In more preferred embodiments, the catalyst has the formula (21) or (22):

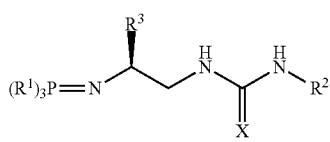
(21)

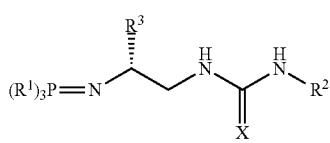
(22)

wherein: $R^1$, $R^2$, $R^3$, and X are as defined above, with the proviso that $R^3$ is not hydrogen;

or the catalyst has the formula (23) or (24):

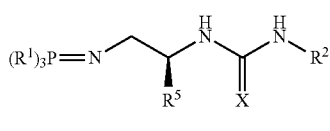
(23)

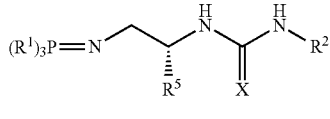
(24)

wherein: $R^1$, $R^2$, $R^5$, and X are as defined above, with the proviso that $R^5$ is not hydrogen;

or the catalyst has the formula (25), (26), (27) or (28):

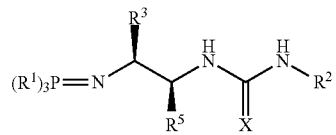
(25)

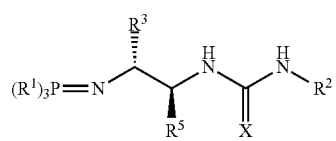
(26)

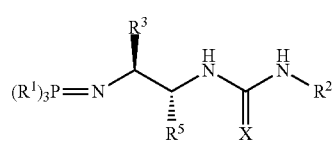
(27)

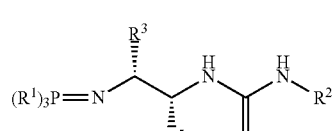
(28)

wherein: $R^1$, $R^2$, $R^3$, $R^5$ and X are as defined above, with the provisos that $R^3$ is not hydrogen and $R^5$ is not hydrogen.

In particularly preferred embodiments, the catalyst has the formula (23) or (24), wherein X is S, $R^1$ is phenyl or 4-methoxyphenyl, $R^2$ is selected from 4-(trifluoromethylphenyl), 3,5-bis-(trifluoromethyl)phenyl and 4-nitrophenyl, and $R^5$ is selected from iso-propyl, tert-butyl, phenyl, benzyl and diphenylmethyl.

Examples of catalysts in accordance with the invention include:

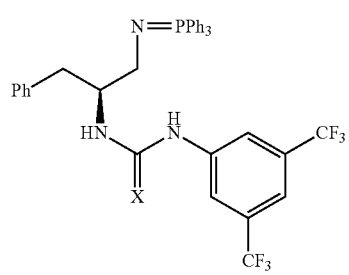
(29a)

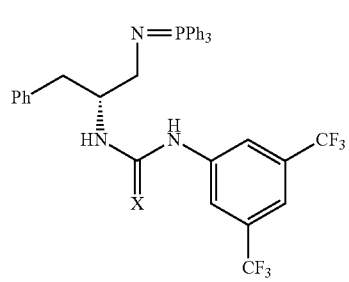
(29b)

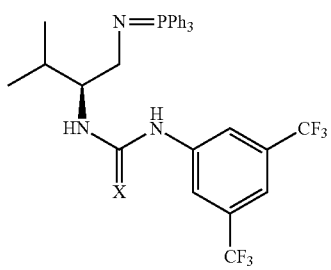
(30a)
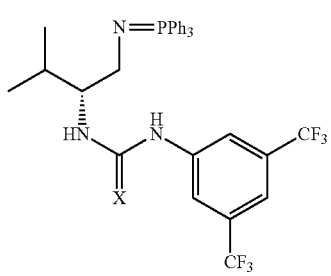
(30b)
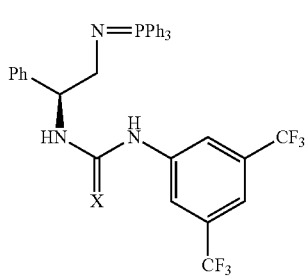
(31a)
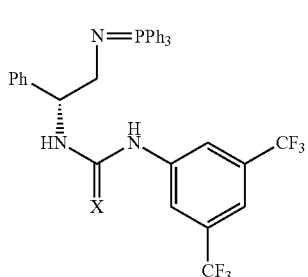
(31b)
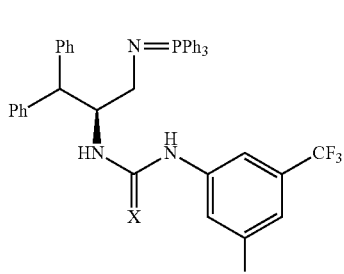
(32a)
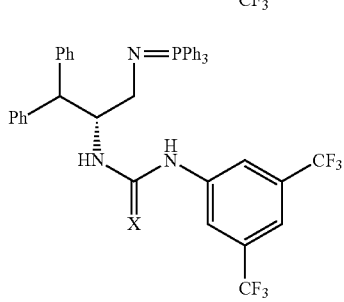
(32b)
(33a)
(33b)
(34a)
(34b)
(35a)
(35b)

-continued
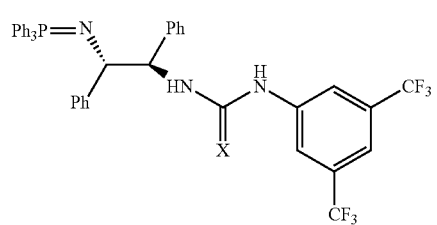 (36a)
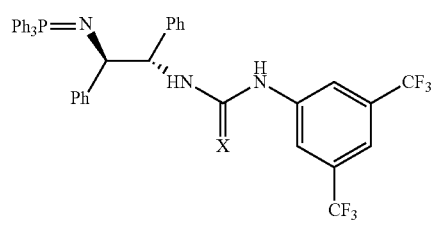 (36b)
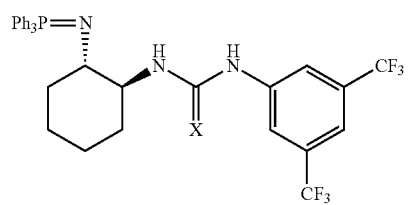 (37a)
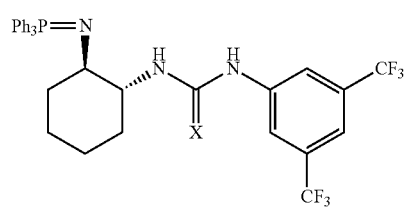 (37b)
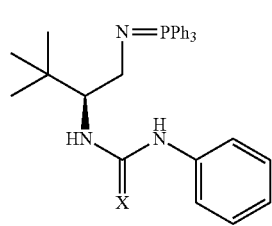 (38a)
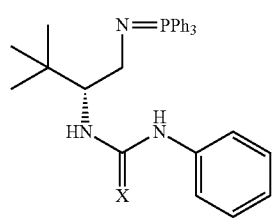 (38b)
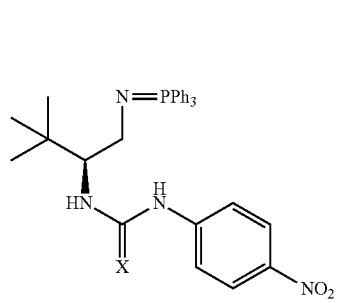 (39a)
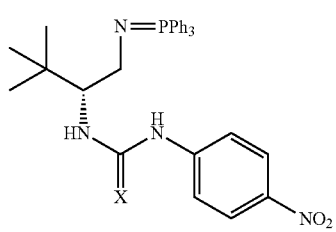 (39b)
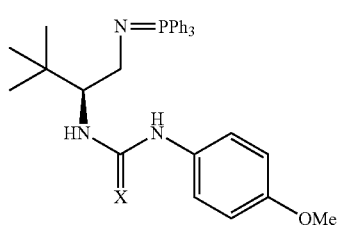 (40a)
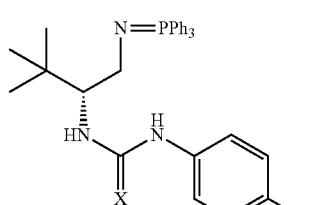 (40b)
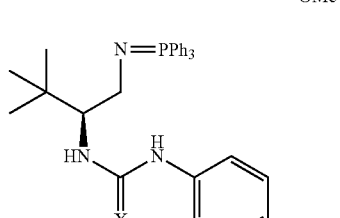 (41a)
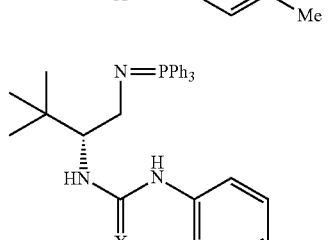 (41b)
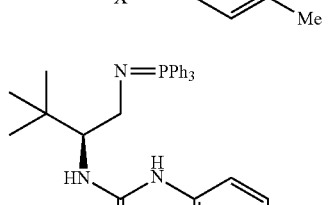 (42a)
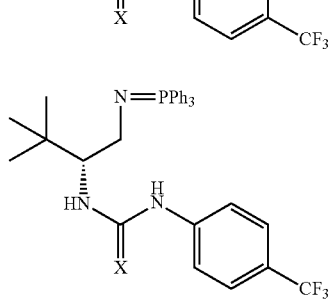 (42b)

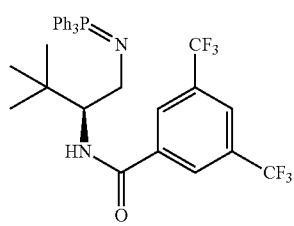
(43a)
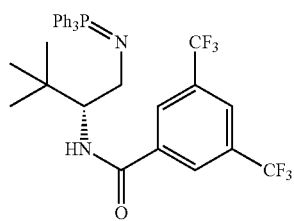
(43b)
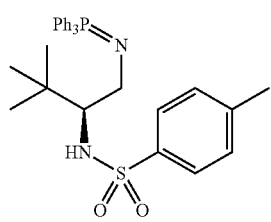
(44a)
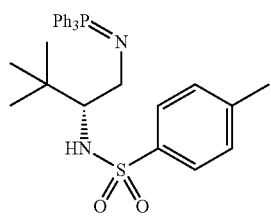
(44b)
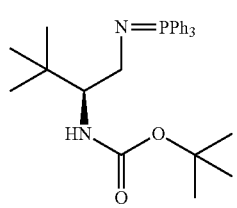
(45a)
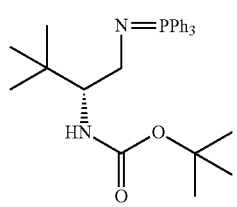
(45b)
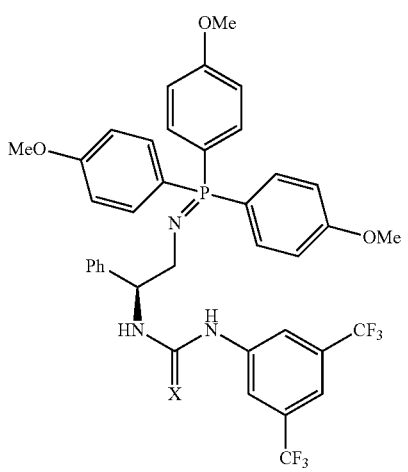
(46a)
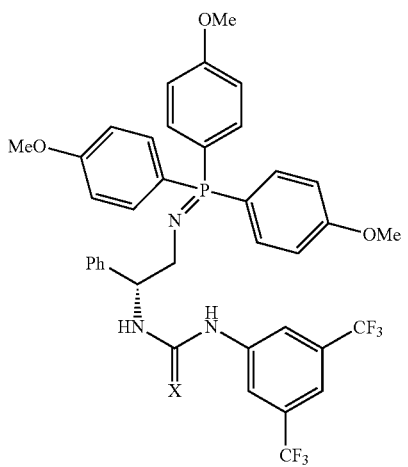
(46b)
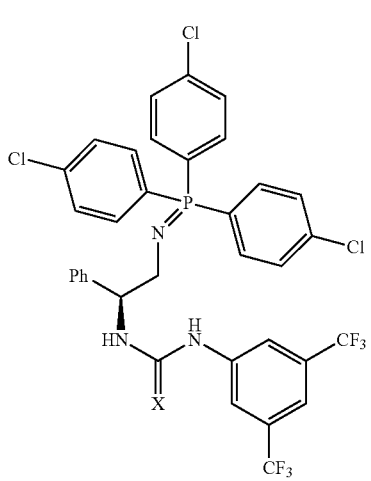
(47a)

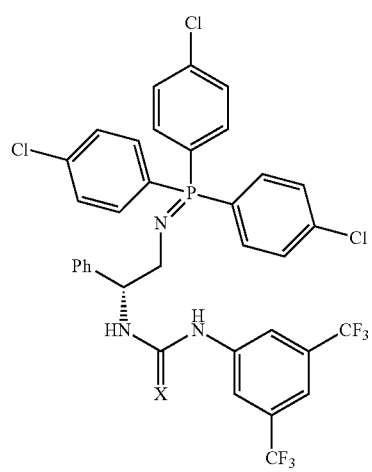
(47b)
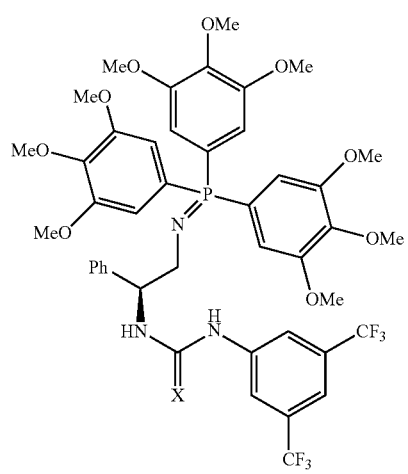
(49a)
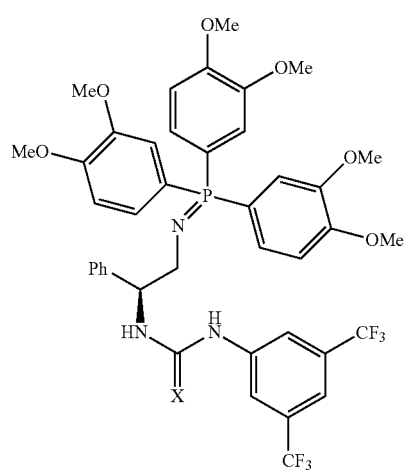
(48a)
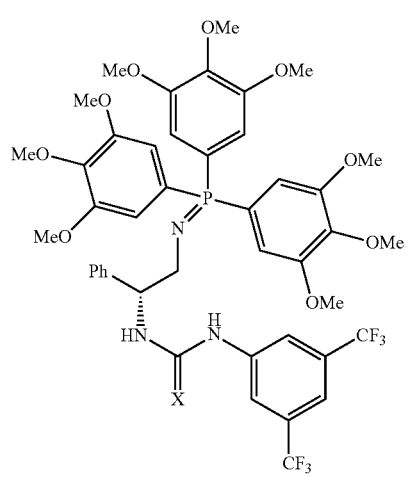
(49b)
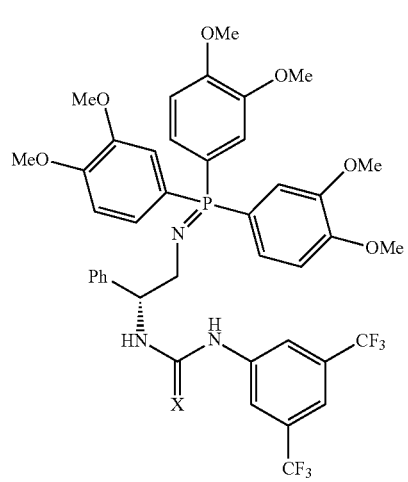
(48b)
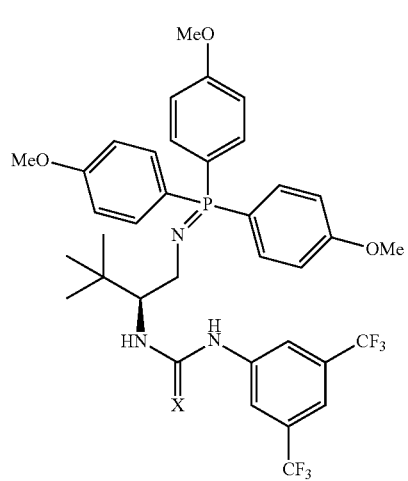
(50a)

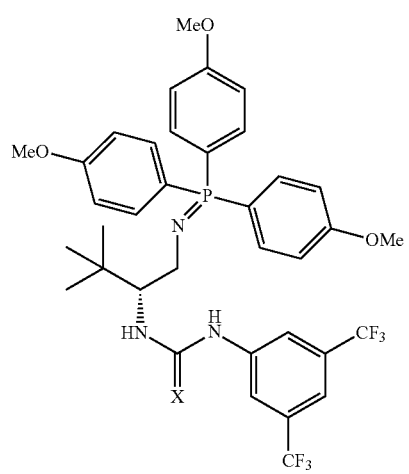
(50b)
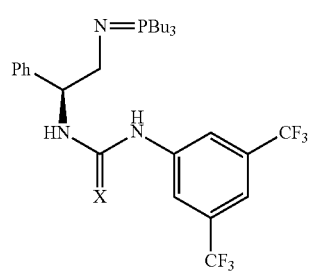
(51a)
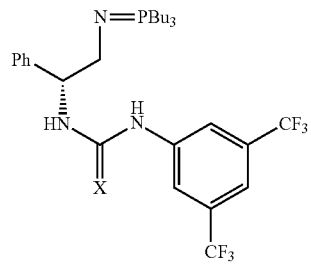
(51b)
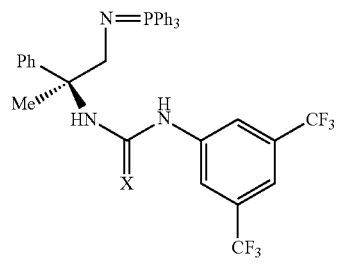
(52a)
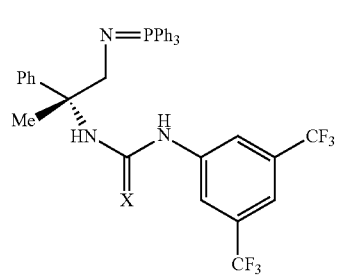
(52b)
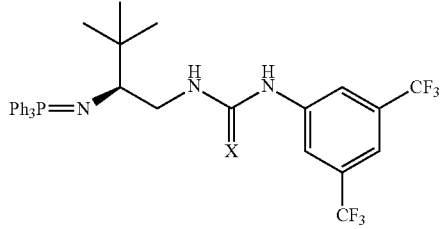
(53a)
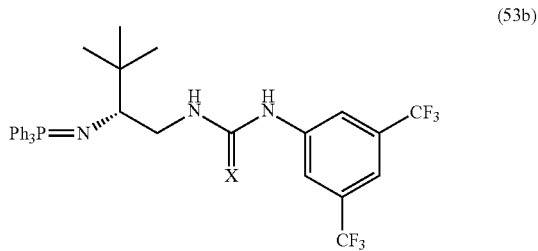
(53b)
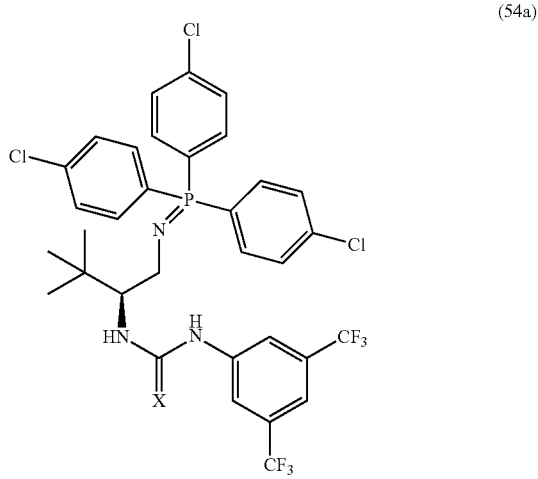
(54a)
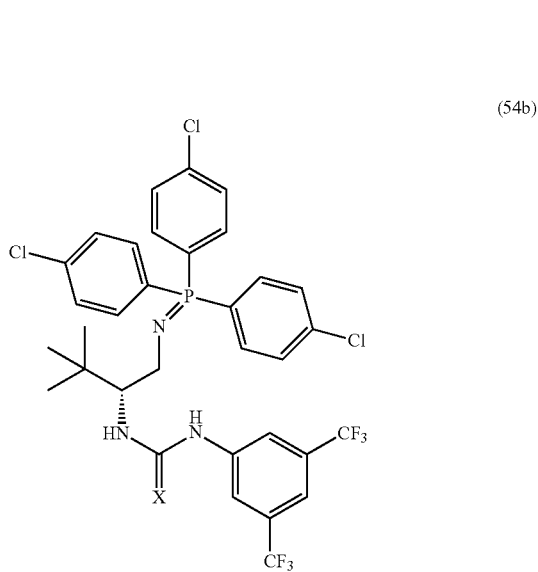
(54b)

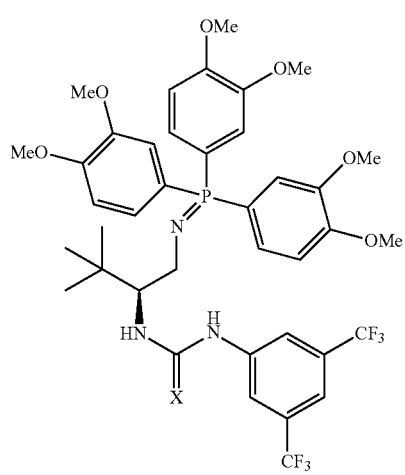
(55a)
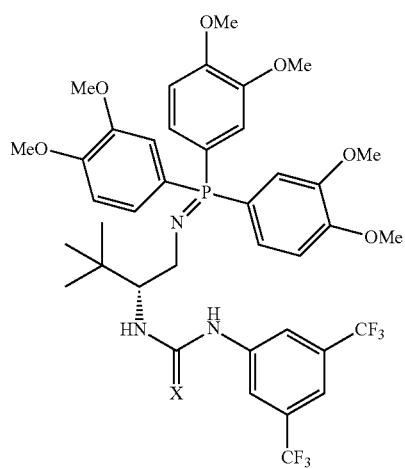
(55b)
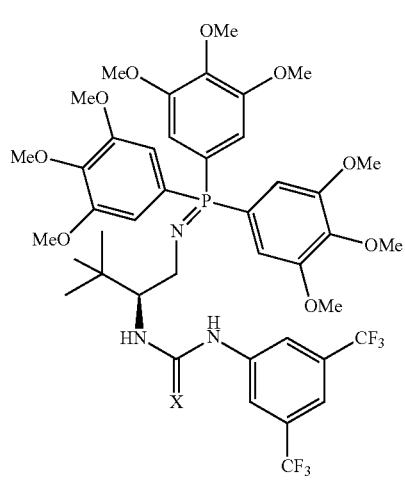
(56a)
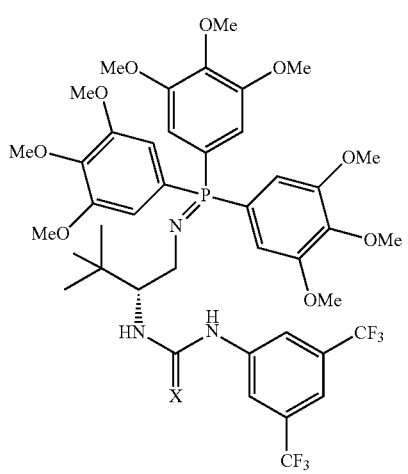
(56b)
wherein X is S or O, and preferably X is S.
Further examples of catalysts in accordance with the invention include:
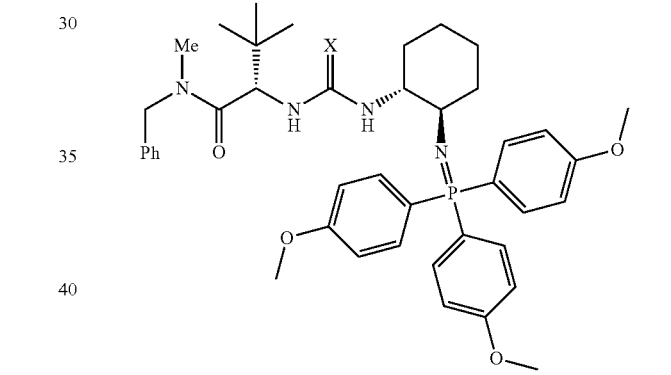
(141a)
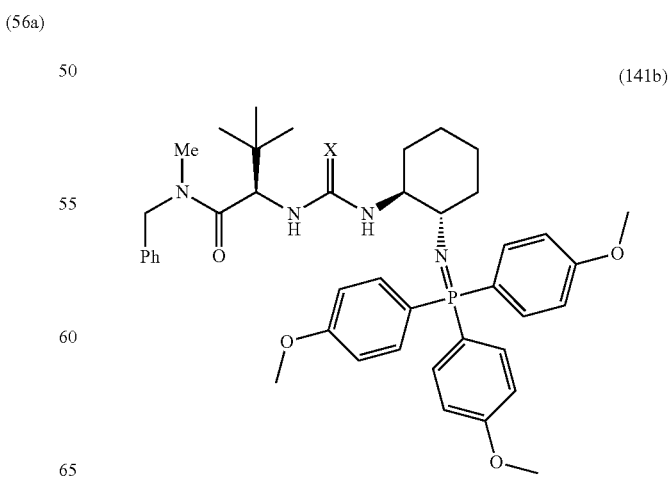
(141b)

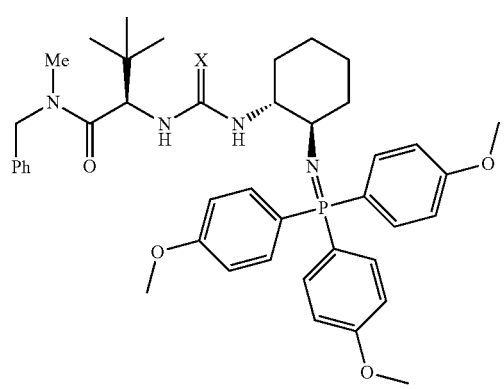
(142a)
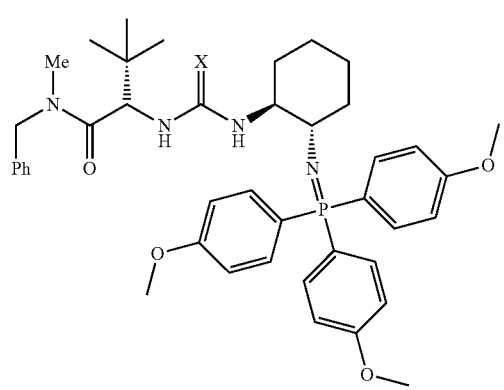
(142b)
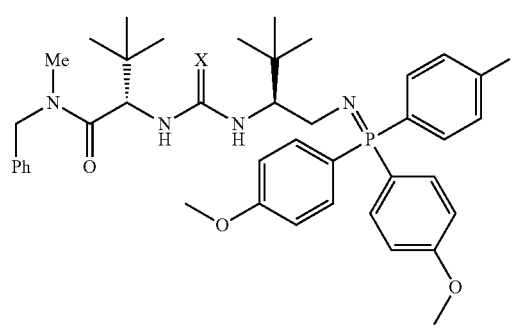
(143a)
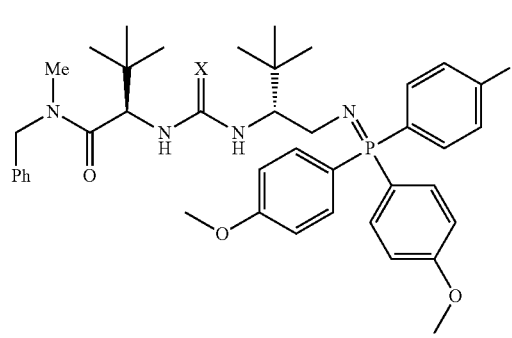
(143b)
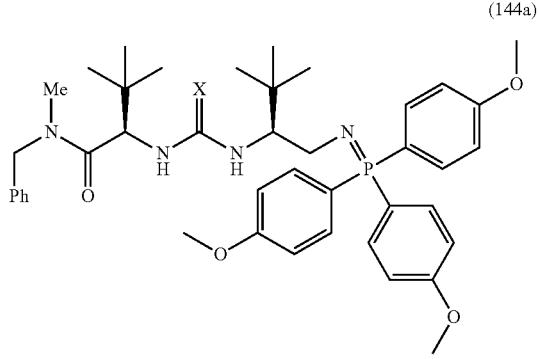
(144a)
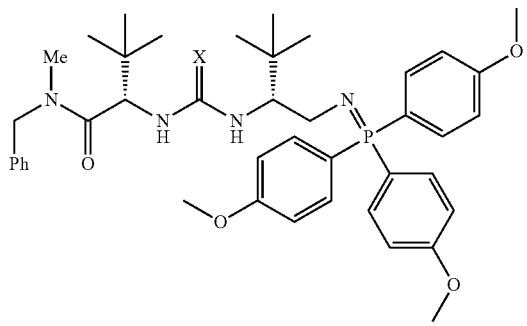
(144b)
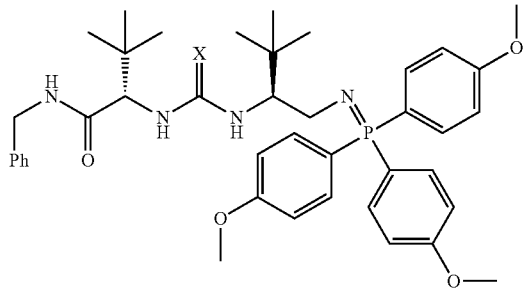
(145a)
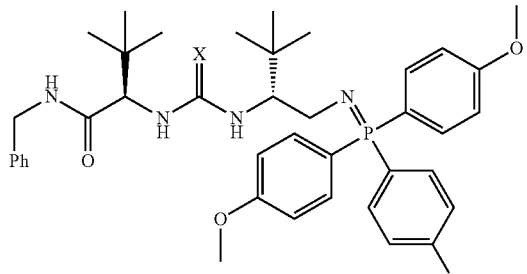
(145b)
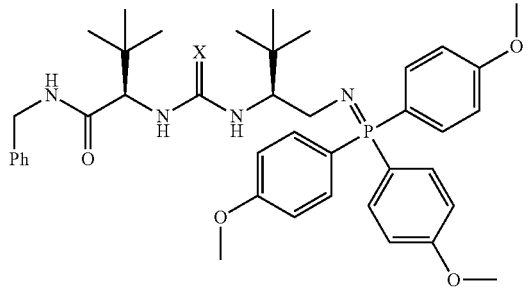
(146a)

-continued
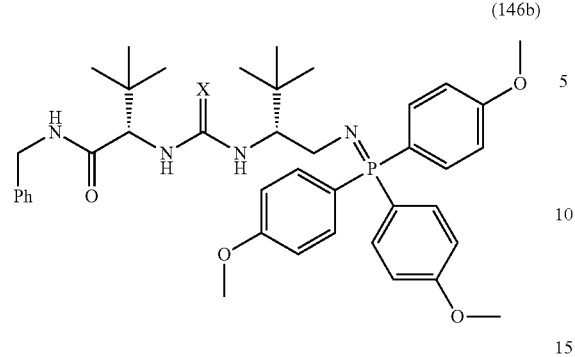
(146b)
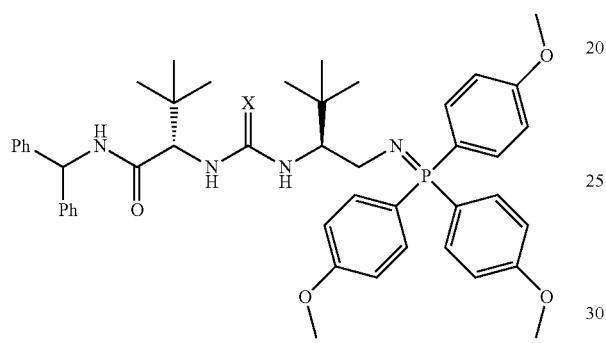
(147a)
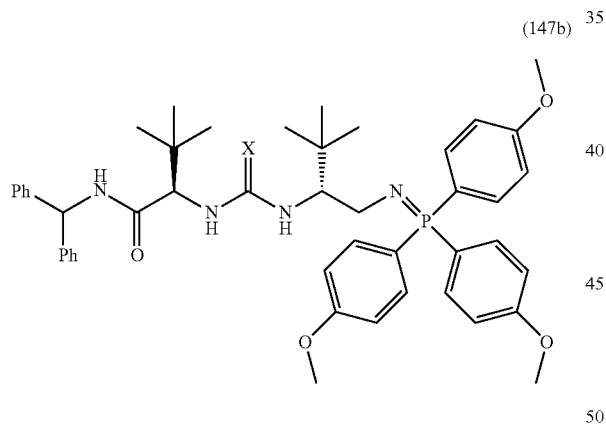
(147b)
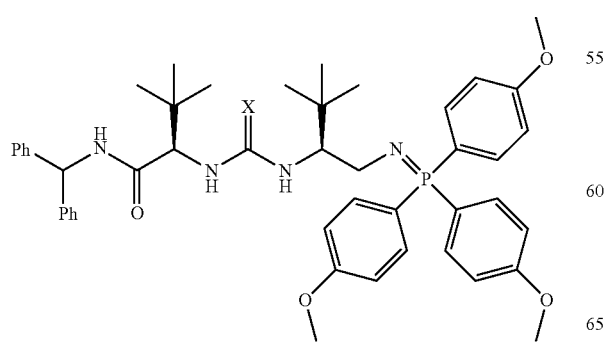
(148a)
-continued
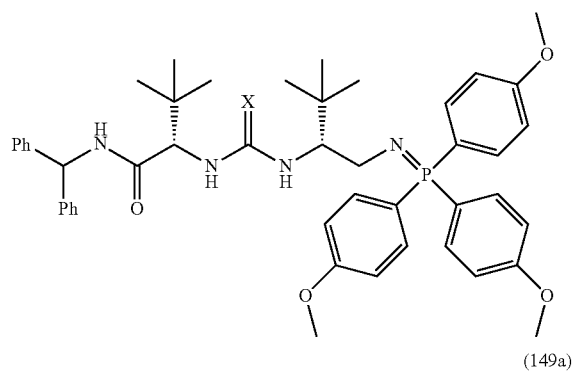
(148b)
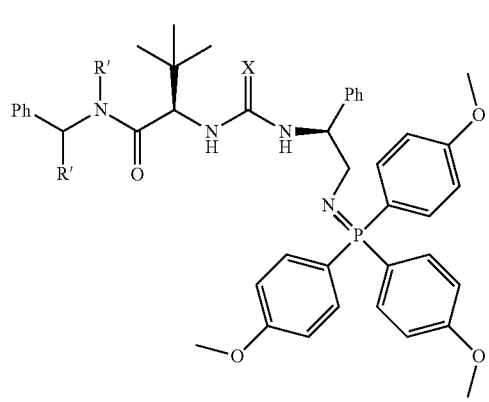
(149a)
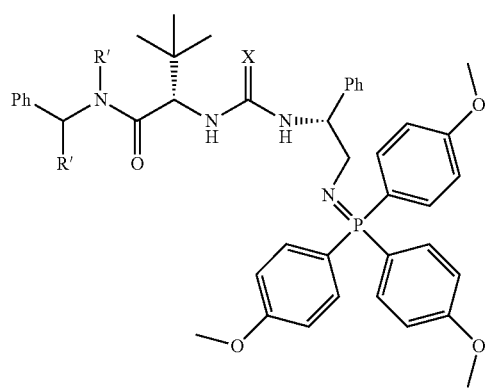
(149b)
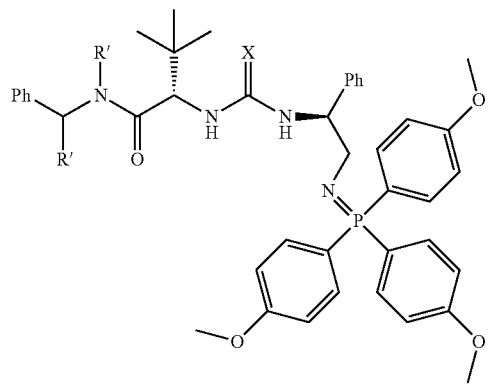
(150a)

-continued
(150b)
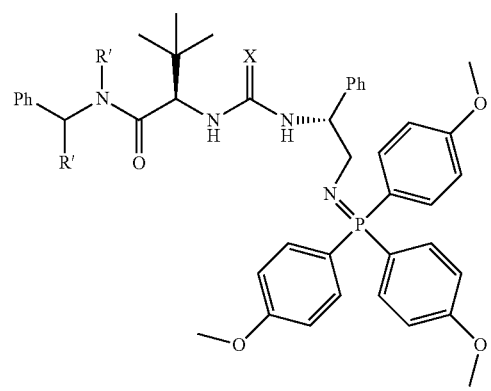
(151a)
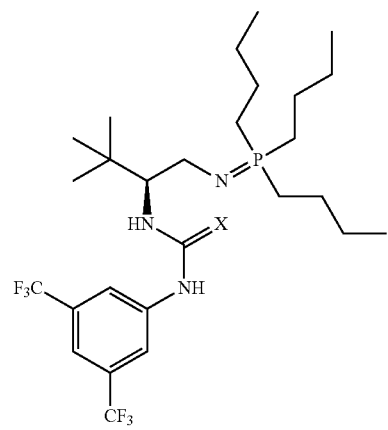
(151b)
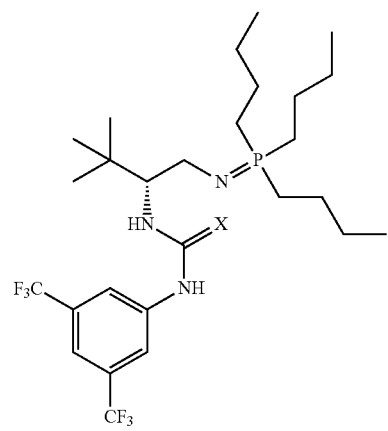
-continued
(152a)
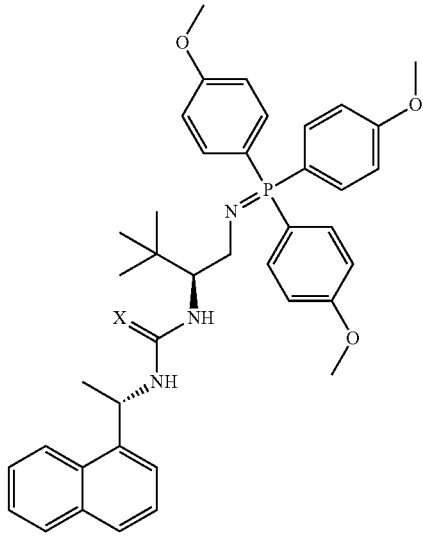
(152b)
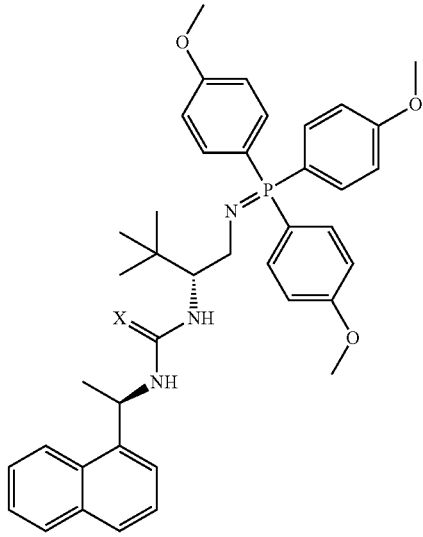
(153a)
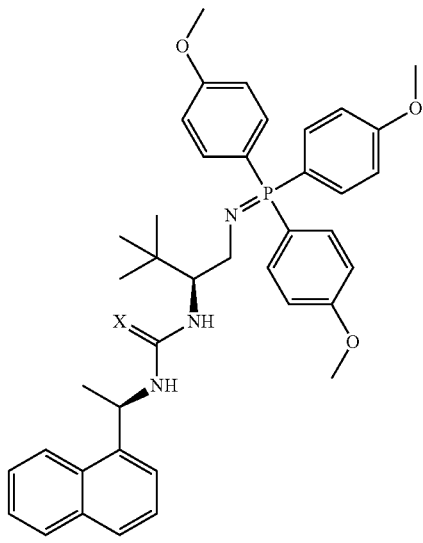

-continued
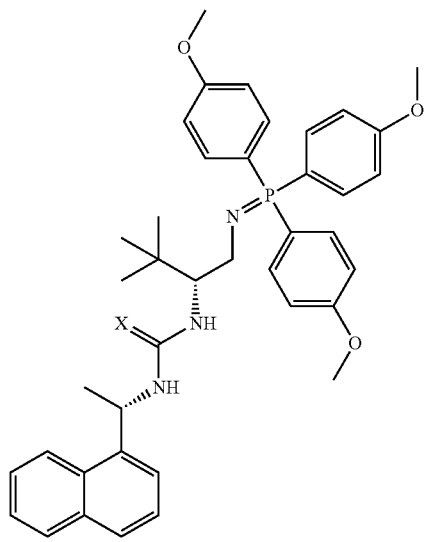
(153b)
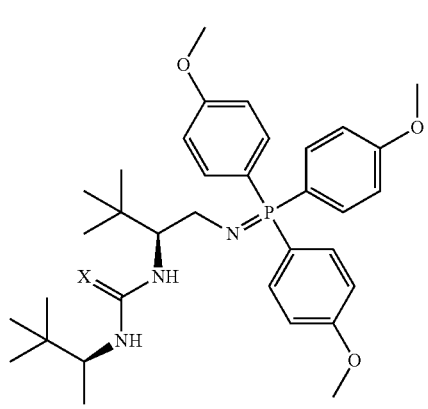
(154a)
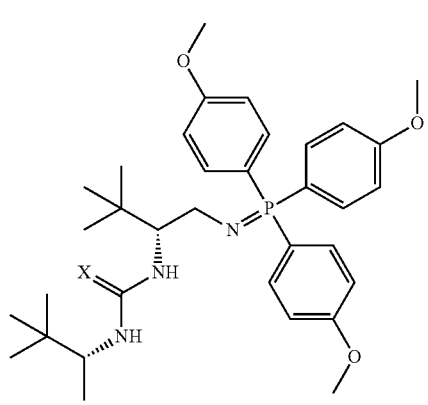
(154b)
-continued
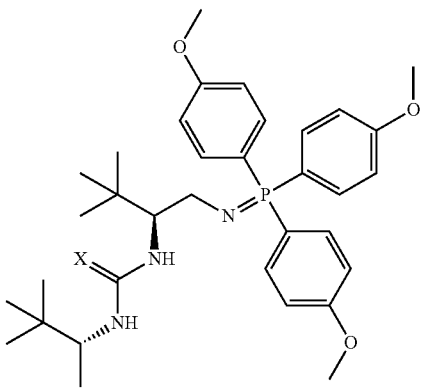
(155a)
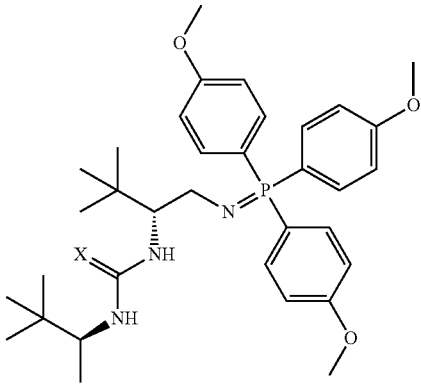
(155b)
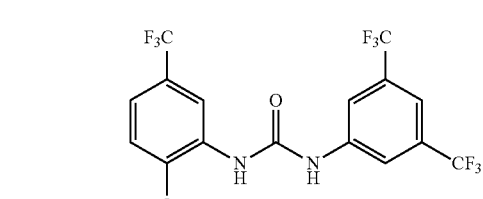
(156a)
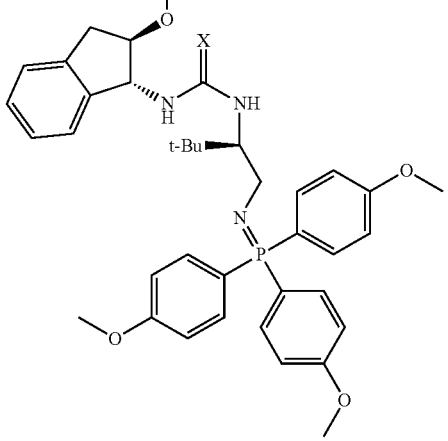

(156b)
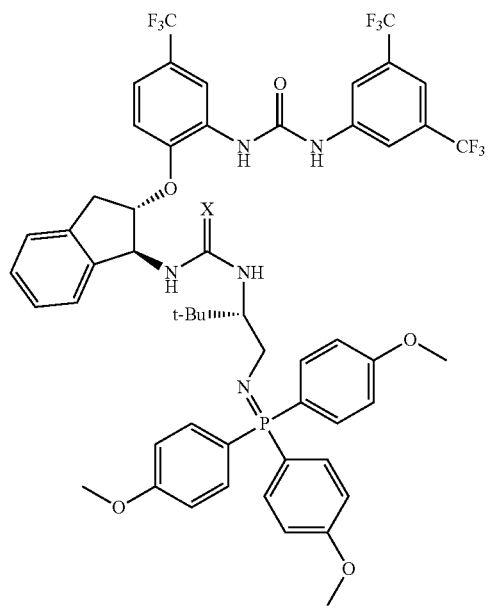
(157b)
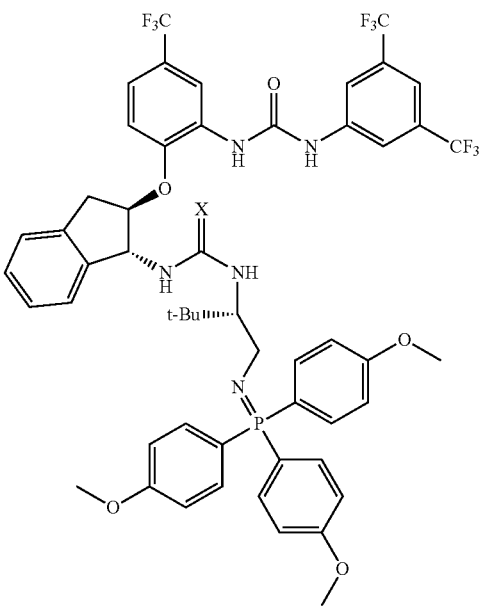
(157a)
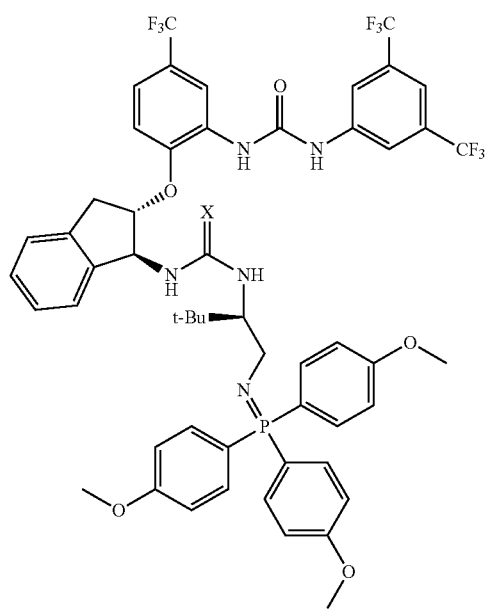
(158a)
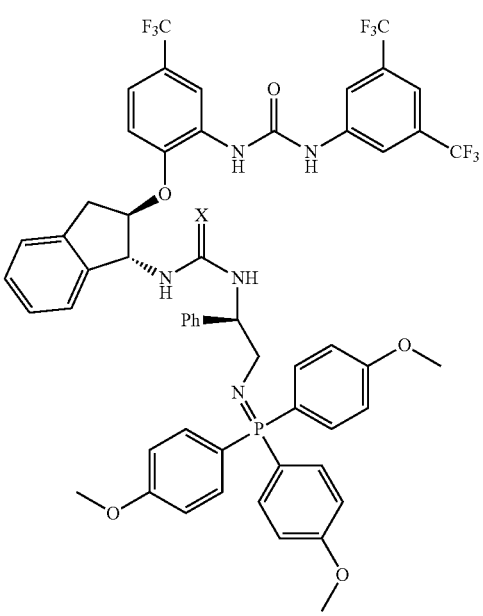

-continued (158b)

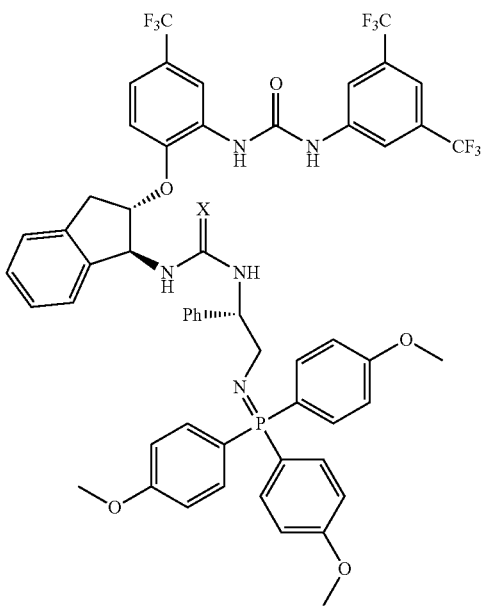

(159b)

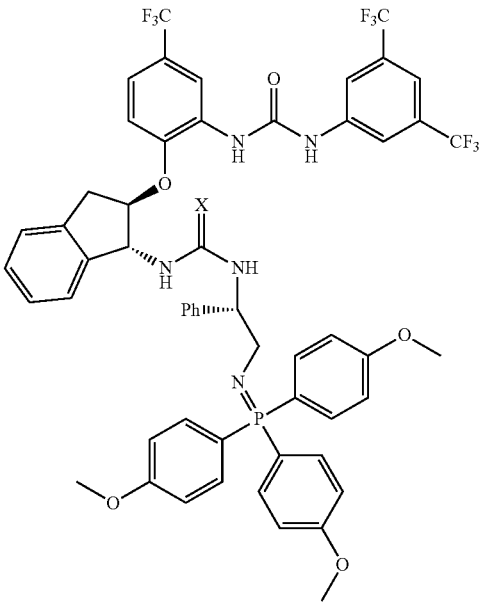

wherein:
X is S or O, and preferably X is S; and
each R' is independently selected from hydrogen, a ($C_1$-$C_{10}$)alkyl group, a ($C_6$-$C_{10}$)aryl group, a ($C_7$-$C_{14}$) aralkyl group and a ($C_7$-$C_{14}$)alkaryl group.

In another aspect, the present invention provides a process for the preparation of the product of an addition reaction, said process comprising reacting a pro-nucleophile with an electrophile in the presence of a catalyst having the formula (1):

$$(R^1)_3P=N-Z-NH-EWG \qquad (1)$$

wherein $R^1$, Z and EWG are as defined above. For the avoidance of doubt, preferred definitions of the compounds of formula (1) as described above (including preferred definitions of $R^1$, Z and EWG) are also preferred in accordance with this aspect of the invention.

In a preferred embodiment, the linking group Z contains one or more stereocentres and the compound of formula (1) is provided as a single stereoisomer.

Where the catalyst is chiral, it has been found that particularly high levels of stereocontrol may be obtained where the hydrogen bond donor is a urea or thiourea group, for example catalysts in which EWG is —C(=O)NHR² or —C(=S)NHR². Thus, in some embodiments EWG is preferably selected from —C(=O)NHR² and —C(=S)NHR², wherein R² is as defined above.

Lower levels of stereocontrol may be observed where the hydrogen bond donor is an amide group (for example where EWG is —C(=O)R²), and racemic products have been obtained where the hydrogen bond donor is a sulfonamide (for example where EWG is —SO₂R²) or a carbamate (for example where EWG is —C(=O)OR²). It is believed that the difference in stereochemical outcomes is due to the increased hydrogen bond donor strength of urea and thiourea hydrogen bond donor groups. However, catalysts with amide, sulfonamide and carbamate groups as H-bond-donors are nonetheless believed to promote the reaction via activation of the pro-nucleophile and may find application in circumstances where enantiomerically-enriched products (159a)

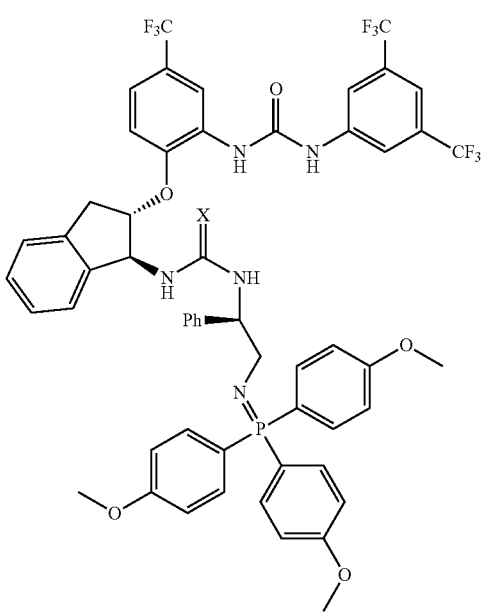

are not required or where an achiral product is formed. Given the ready availability of precursors of the linking moiety Z from the chiral pool, it may nonetheless be preferable to use a chiral linking moiety Z even where the hydrogen bond donor is an amide, sulfonamide or carbamate.

Preferably, the catalyst has the formula (2) or (3) as defined above. More preferably, the catalyst has the formula (3) as defined above.

Preferably the catalyst of formula (2) or (3) is a single stereoisomer wherein at least one of $R^3$, $R^4$ and $R^5$ is not hydrogen, more preferably at least one of $R^3$ and $R^5$ is not hydrogen, and most preferably $R^5$ is not hydrogen.

In further embodiments, the catalyst has the formula (5) or (6):

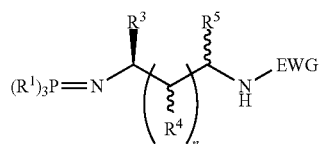

(5)

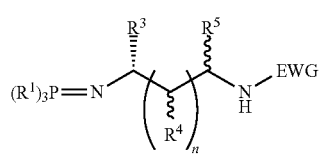

(6)

wherein: $R^1$, $R^3$, each $R^4$, $R^5$, EWG and n are as defined above, with the proviso that $R^3$ is not hydrogen;

or the catalyst has the formula (7) or (8):

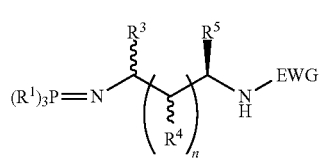

(7)

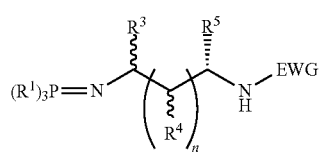

(8)

wherein: $R^1$, $R^3$, each $R^4$, $R^5$, EWG and n are as defined above, with the proviso that $R^5$ is not hydrogen.

In further embodiments, the catalyst has the formula (9) or (10):

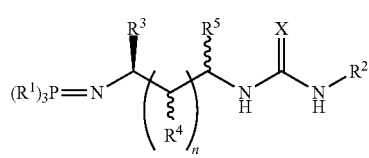

(9)

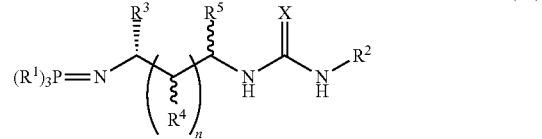

(10)

wherein: $R^1$, $R^2$, $R^3$, each $R^4$, $R^5$, X and n are as defined above, with the proviso that $R^3$ is not hydrogen;

or the catalyst has the formula (11) or (12):

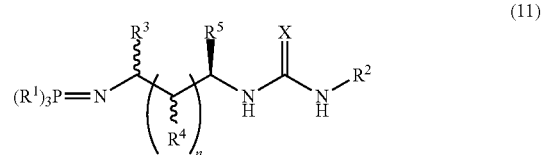

(11)

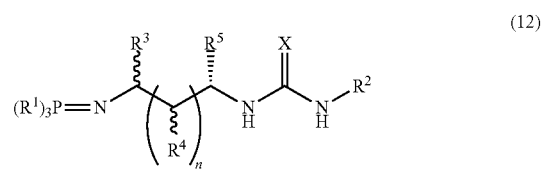

(12)

wherein: $R^1$, $R^2$, $R^3$, each $R^4$, $R^5$, X and n are as defined above, with the proviso that $R^5$ is not hydrogen.

In preferred embodiments, the catalyst has the formula (13) or (14):

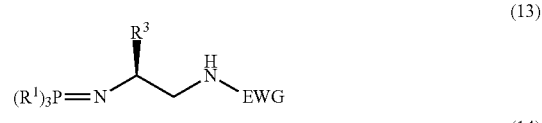

(13)

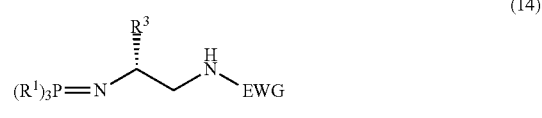

(14)

wherein: $R^1$, $R^3$ and EWG are as defined above, with the proviso that $R^3$ is not hydrogen;

or the catalyst has the formula (15) or (16):

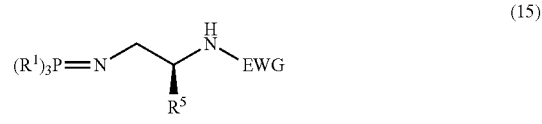

(15)

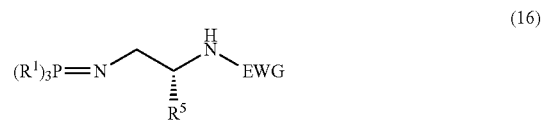

(16)

wherein: $R^1$, $R^5$ and EWG are as defined above, with the proviso that $R^5$ is not hydrogen;

or the catalyst has the formula (17), (18), (19) or (20):

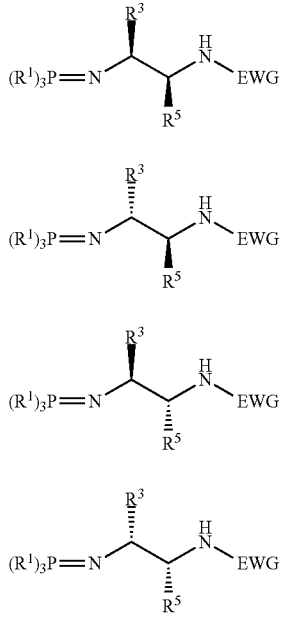

wherein: $R^1$, $R^3$, $R^5$ and EWG are as defined above, with the provisos that $R^3$ is not hydrogen and $R^5$ is not hydrogen.

In more preferred embodiments, the catalyst has the formula (21) or (22):

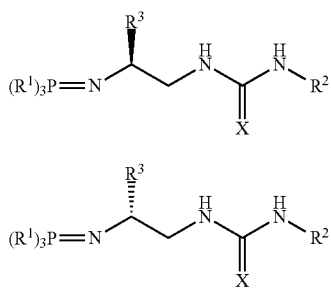

wherein: $R^1$, $R^2$, $R^3$ and X are as defined above, with the proviso that $R^3$ is not hydrogen;

or the catalyst has the formula (23) or (24):

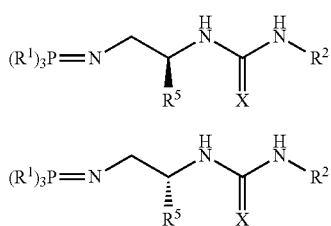

wherein: $R^1$, $R^2$, $R^5$ and X are as defined above, with the proviso that $R^5$ is not hydrogen;

or the catalyst has the formula (25), (26), (27) or (28):

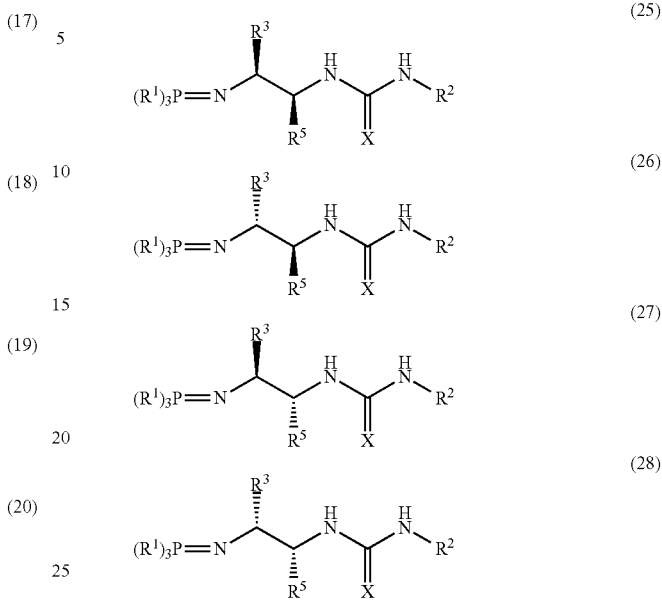

wherein: $R^1$, $R^2$, $R^3$, $R^5$ and X are as defined above, with the proviso that $R^3$ is not hydrogen and $R^5$ is not hydrogen.

In particularly preferred embodiments, the catalyst has the formula (23) or (24), wherein X is S, $R^1$ is phenyl or 4-methoxyphenyl, $R^2$ is selected from 4-(trifluoromethylphenyl), 3,5-bis-(trifluoromethyl)phenyl and 4-nitrophenyl, and $R^5$ is selected from iso-propyl, tert-butyl, phenyl, benzyl and diphenylmethyl.

As used herein, the term "pro-nucleophile" refers in general to a species containing an acidic proton which forms a nucleophile via deprotonation. In some embodiments, the nucleophile may be a carbon nucleophile, a nitrogen nucleophile, an oxygen nucleophile, a sulfur nucleophile or a phosphorus nucleophile. Preferably, the nucleophile is a carbon nucleophile.

The reaction is preferably an addition reaction of a nucleophile to a π-bond. In some embodiments, the reaction may be an addition reaction of a nucleophile to a carbon-heteroatom π-bond, and more preferably a carbon-heteroatom double bond. In other embodiments, the reaction may be an addition reaction of a nucleophile to a carbon-carbon multiple bond in conjugation with an electron withdrawing group, and more preferably a carbon-carbon double bond in conjugation with a carbon-heteroatom double bond (Michael addition).

In preferred embodiments, the pro-nucleophile may be selected from ketones, esters, thioesters, sulfones, phosphonates, phosphine oxides nitriles and nitro compounds having an α-carbon atom bearing at least one acidic hydrogen atom.

Examples of suitable pro-nucleophiles include those having the formula (57) or (58):

wherein: $Y^1$ is selected from —$NO_2$, —$C(O)R^8$, —$C(O)OR^8$, —$C(O)SR^8$, —CN and —$SO_2R^8$, $Y^2$ is selected from —$C(O)R^8$, —$C(O)OR^8$, —$C(O)SR^8$, —$P(O)(OR^8)_2$, —$P(O)R^8{}_2$ and —ON; $R^6$ and $R^7$ are independently selected from hydrogen, optionally substituted alkyl, optionally substituted alkenyl, optionally substituted aryl, optionally substituted heteroaryl, optionally substituted alkaryl and optionally substituted aralkyl; and $R^8$ is selected from optionally substituted alkyl, optionally substituted alkenyl, optionally substituted aryl, optionally substituted heteroaryl, optionally substituted alkaryl and optionally substituted aralkyl; or $R^8$ together with $R^6$ or $R^7$ may form a methylene chain having the formula —$(CH_2)_m$—, wherein m is an integer from 1 to 5.

$Y^1$ is preferably —$NO_2$, —$C(O)R^8$ or —$C(O)OR^8$.

$Y^2$ is preferably —$C(O)OR^8$.

$R^6$ and $R^7$ are preferably independently selected from hydrogen, optionally substituted ($C_1$-$C_{20}$)alkyl, optionally substituted ($C_1$-$C_{20}$)alkenyl, optionally substituted ($C_6$-$C_{20}$)aryl, optionally substituted ($C_7$-$C_{20}$)alkaryl and optionally substituted ($C_7$-$C_{20}$)aralkyl groups. For example, $R^6$ and $R^7$ may be independently selected from hydrogen, methyl, ethyl, n-propyl, phenyl, 4-methylphenyl and benzyl.

$R^7$ is preferably hydrogen.

$R^8$ is preferably selected from ($C_1$-$C_{20}$)alkyl, ($C_1$-$C_{20}$)alkenyl, ($C_6$-$C_{20}$)aryl, ($C_7$-$C_{20}$)alkylaryl and ($C_7$-$C_{20}$)arylalkyl groups. For example, $R^8$ may be selected from methyl, ethyl, n-propyl, n-butyl, sec-butyl, iso-butyl, tert-butyl, phenyl and benzyl.

In a preferred embodiment, the pro-nucleophile has the formula (57) and $Y^1$ is —$NO_2$. For example, the pro-nucleophile may be nitromethane.

In another embodiment, the pro-nucleophile is an imidate, preferably selected from compounds having the formula (159):

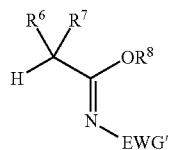

(159)

wherein: $R^6$, $R^7$ and $R^8$ are as defined above; and EWG' represents an electron-withdrawing group. EWG' is preferably selected from groups having the formula —C(=X)$NHR^2$, —C(=X)$R^2$, —$SO_2R^2$ and —C(=X)$XR^2$, wherein X is selected from O and S, and wherein $R^2$ is selected from an optionally substituted ($C_1$-$C_{10}$)alkyl group, an optionally substituted ($C_3$-$C_{10}$)cycloalkyl group, an optionally substituted ($C_6$-$C_{10}$)aryl group, an optionally substituted ($C_7$-$C_{14}$)aralkyl group and an optionally substituted ($C_7$-$C_{14}$)alkaryl group. EWG' preferably has the formula —$SO_2R^2$.

Where $R^2$ is substituted, preferred substituents include ($C_1$-$C_4$)alkoxy, —F, —Cl, —Br, —I, —$CF_3$, —$C_2F_5$ and —$NO_2$.

Other suitable pro-nucleophiles include amines, hydrazines, alcohols, oximes and thiols. For example, the pro-nucleophile may be selected from compounds having the formula (59), (60), (61), (62) or (63):

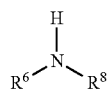

(59)

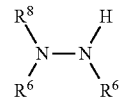

(60)

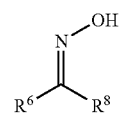

(61)

$R^8$—OH (62)

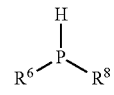

(63)

$R^8$—SH wherein $R^6$ and $R^8$ are as defined above.

Other heteroatom-centered acids may also be used as pro-nucleophiles, such as phosphites, phosphines and sulphites. For example, the pro-nucleophile may be selected from compounds having the formula (160), (161) or (162):

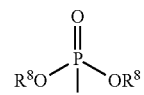

(160)

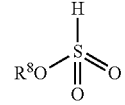

(161)

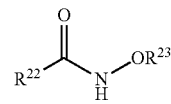

(162)

wherein $R^6$ and $R^8$ are as defined above.

Further suitable pro-nucleophiles include hydroxamic acids, preferably selected from compounds having the formula (163):

(163)

wherein: $R^{22}$ is selected from optionally substituted ($C_1$-$C_{20}$)alkyl, optionally substituted ($C_1$-$C_{20}$)alkenyl, optionally substituted ($C_6$-$C_{20}$)aryl, optionally substituted ($C_7$-$C_{20}$)alkaryl, optionally substituted ($C_7$-$C_{20}$)aralkyl and optionally substituted ($C_1$-$C_{10}$) alkoxy groups; and $R^{23}$ is selected from hydrogen, optionally substituted ($C_1$-$C_{20}$)alkyl, optionally substituted ($C_1$-$C_{20}$)alkenyl, optionally substituted ($C_6$-$C_{20}$)aryl, optionally substituted ($C_7$-$C_{20}$)alkaryl, optionally substituted ($C_7$-$C_{20}$)aralkyl groups and protecting groups;

$R^{22}$ is preferably an unsubstituted ($C_1$-$C_{10}$) alkoxy group. $R^{23}$ is preferably selected from unsubstituted ($C_1$-$C_{10}$)alkyl groups and protecting groups. The protecting group may be a silyl protecting group such as a silyl ether.

In an embodiment, the pro-nucleophile is a heterocyclic compound. The heterocyclic compound may be saturated (e.g. heterocycloalkyl) or unsaturated (e.g. heteroaryl), but it is preferably unsaturated. The heterocyclic compound may have from 4 to 16 ring atoms, e.g. from 4 to 10 ring atoms. The ring atoms include at least one ring carbon atom and at least one protonated ring heteroatom selected from nitrogen and phosphorus. Other heteroatoms such as oxygen and sulphur may also be present as a ring atom. Examples of suitable saturated heterocyclic compounds include pyrrolidine, phospholane, imidazolidine, pyrazolidine, oxazolidine, thiazolidine, piperidine, phosphinane, piperazine, morpholine, thiomorpholine, azepane and homopiperazine. Examples of suitable unsaturated heterocyclic compounds include pyrrole, phosphole, imidazole, pyrazole, triazole, tetrazole, oxazine, thiazine, azepine, diazepine and benzotriazole. Preferred heterocycles include pyrrole, imidazole, pyrazole, triazole, tetrazole and benzotriazole.

The electrophile is preferably selected from aldehydes, ketones, esters, aldimines, ketimines, amides, α,β-unsaturated aldehydes, α,β-unsaturated ketones, α,β-unsaturated esters, α,β-unsaturated aldimines, α,β-unsaturated ketimines, α,β-unsaturated amides, α,β-unsaturated nitriles, α,β-unsaturated nitro compounds and α,β-unsaturated sulfoxides.

Examples of suitable electrophiles include those having the formula (64), (65) or (66):

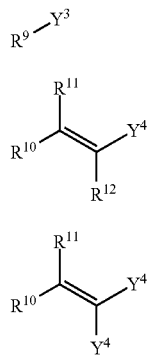

wherein:
$R^9$ is selected from optionally substituted alkyl, optionally substituted alkenyl, optionally substituted aryl, optionally substituted heteroaryl, optionally substituted alkaryl and optionally substituted aralkyl groups;

$R^{10}$, $R^{11}$ and $R^{12}$ are independently selected from hydrogen, optionally substituted alkyl, optionally substituted alkenyl, optionally substituted aryl, optionally substituted heteroaryl, optionally substituted alkaryl and optionally substituted aralkyl groups, or $R^{10}$ together with $R^{11}$ may form a methylene chain having the formula —$(CH_2)_p$—, wherein p is an integer from 2 to 5, or $R^{10}$ together with $R^{12}$ may form a methylene chain having the formula —$(CH_2)_m$—, wherein m is an integer from 1 to 5;

$Y^3$ is selected from —$C(O)R^{13}$, —$C(O)OR^{14}$, —$C(=NR^{15})R^{13}$ and —$C(O)NR^{16}R^{17}$, each $Y^4$ is independently selected from —$C(O)R^{13}$, —$C(O)OR^{14}$, —$C(=NR^{15})R^{13}$, —$C(O)NR^{16}R^{17}$, —CN, —$NO_2$ and —$S(O)R^{13}$;

$R^{13}$ is selected from hydrogen, optionally substituted alkyl, optionally substituted alkenyl, optionally substituted aryl, optionally substituted heteroaryl, optionally substituted alkaryl and optionally substituted aralkyl, or $R^{13}$ together with $R^9$ or $R^{11}$ may form a methylene chain having the formula —$(CH_2)_p$—, wherein p is an integer from 2 to 5, or $R^{13}$ together with $R^{12}$ may form a methylene chain having the formula —$(CH_2)_m$—, wherein m is an integer from 1 to 5;

$R^{14}$ is selected from optionally substituted alkyl, optionally substituted alkenyl, optionally substituted aryl, optionally substituted heteroaryl, optionally substituted alkaryl and optionally substituted aralkyl; or $R^{14}$ together with $R^9$, $R^{11}$ or $R^{12}$ may form a methylene chain having the formula —$(CH_2)_m$—, wherein m is an integer from 1 to 5;

$R^{15}$ is selected from optionally substituted alkyl, optionally substituted alkenyl, optionally substituted aryl, optionally substituted heteroaryl, optionally substituted alkaryl, optionally substituted aralkyl, a group of the formula —$P(O)(R^{18})_2$, a group of the formula —$C(O)R^{18}$, a group of the formula —$C(O)OR^{18}$ and a group of the formula —$S(O)_2R^{18}$, $R^{16}$ and $R^{17}$ are independently selected from hydrogen, optionally substituted alkyl, optionally substituted alkenyl, optionally substituted aryl, optionally substituted heteroaryl, optionally substituted alkaryl and optionally substituted aralkyl groups, or $R^{16}$ and $R^{17}$ may together form a methylene chain having the formula —$(CH_2)_p$—, a chain of the formula —$C(O)(CH_2)_p$— or a chain of the formula —$C(O)O(CH_2)_p$—, wherein p is an integer of from 2 to 5, or one of $R^{16}$ and $R^{17}$ together with any one of $R^9$, $R^{11}$ and $R^{12}$ may together form a methylene chain having the formula —$(CH_2)_p$—, wherein p is an integer from 2 to 5; and $R^{18}$ is selected from optionally substituted alkyl, optionally substituted alkenyl, optionally substituted aryl, optionally substituted heteroaryl, optionally substituted alkaryl and optionally substituted aralkyl groups.

In preferred embodiments, $Y^3$ is —$C(O)R^{13}$ or —$C(O)OR^{14}$.

In further preferred embodiments, $Y^3$ is —$C(=NR^{15})R^{13}$.

In preferred embodiments, each $Y^4$ is independently selected from —$C(O)R^{13}$, —$C(O)OR^{14}$, —$C(O)NR^{16}R^{17}$ and —$NO_2$.

$R^9$ is preferably selected from an optionally substituted $(C_1$-$C_{10})$alkyl group, an optionally substituted $(C_3$-$C_{10})$cycloalkyl group, an optionally substituted $(C_6$-$C_{10})$aryl group, an optionally substituted $(C_4$-$C_9)$heteroaryl group, an optionally substituted $(C_7$-$C_{14})$aralkyl group and an optionally substituted $(C_7$-$C_{14})$alkaryl group, or $R^9$ together with $R^{13}$, $R^{14}$, $R^{16}$ or $R^{17}$ forms a methylene chain having the formula —$(CH_2)_m$—, wherein m is an integer of from 3 to 5.

$R^{10}$, $R^{11}$ and $R^{12}$ are preferably independently selected from hydrogen, an optionally substituted $(C_1$-$C_{10})$alkyl group, an optionally substituted $(C_3$-$C_{10})$cycloalkyl group, an optionally substituted $(C_6$-$C_{10})$aryl group, an optionally substituted $(C_4$-$C_9)$heteroaryl group, an optionally substituted $(C_7$-$C_{14})$aralkyl group and an optionally substituted $(C_7$-$C_{14})$alkaryl group, or $R^{11}$ together with $R^{13}$, $R^{14}R^{16}$ or $R^{17}$ forms a methylene chain having the formula —$(CH_2)_m$—, wherein m is an integer of from 3 to 5.

$R^{13}$ is preferably selected from an optionally substituted $(C_1$-$C_{10})$alkyl group, an optionally substituted $(C_3$-$C_{10})$cycloalkyl group, an optionally substituted $(C_6$-$C_{10})$aryl group, an optionally substituted $(C_4$-$C_9)$heteroaryl group, an optionally substituted $(C_7$-$C_{14})$aralkyl group and an optionally substituted $(C_7$-$C_{14})$alkaryl group, or $R^{13}$ together with $R^9$ or $R^{11}$ forms a methylene chain having the formula —$(CH_2)_p$—, wherein p is an integer from 3 to 5, or $R^{13}$ together with $R^{12}$ forms a methylene chain having the formula —$(CH_2)_m$—, wherein m is an integer from 3 to 5.

$R^{14}$ is preferably selected from an optionally substituted $(C_1\text{-}C_{10})$alkyl group, an optionally substituted $(C_3\text{-}C_{10})$cycloalkyl group, an optionally substituted $(C_6\text{-}C_{10})$aryl group, an optionally substituted $(C_7\text{-}C_{14})$aralkyl group and an optionally substituted $(C_7\text{-}C_{14})$alkaryl group, or $R^{14}$ together with $R^9$, $R^{11}$ or $R^{12}$ forms a methylene chain having the formula $-(CH_2)_m-$, wherein m is an integer from 3 to 5.

$R^{15}$ is preferably independently selected from an optionally substituted $(C_1\text{-}C_{10})$alkyl group, an optionally substituted $(C_3\text{-}C_{10})$cycloalkyl group, an optionally substituted $(C_6\text{-}C_{10})$aryl group, an optionally substituted $(C_4\text{-}C_9)$heteroaryl group, an optionally substituted $(C_7\text{-}C_{14})$aralkyl group, an optionally substituted $(C_7\text{-}C_{14})$alkaryl group, a group of the formula $-P(O)(R^{18})_2$, a group of the formula $-C(O)R^{18}$, a group of the formula $-C(O)OR^{18}$ and a group of the formula $-S(O)_2R^{18}$.

$R^{16}$ and $R^{17}$ are preferably independently selected from hydrogen, an optionally substituted $(C_1\text{-}C_{10})$alkyl group, an optionally substituted $(C_3\text{-}C_{10})$cycloalkyl group, an optionally substituted $(C_6\text{-}C_{10})$aryl group, an optionally substituted $(C_7\text{-}C_{14})$aralkyl group and an optionally substituted $(C_7\text{-}C_{14})$alkaryl group, or $R^{16}$ and $R^{17}$ may together form a methylene chain having the formula $-(CH_2)_p-$, a chain of the formula $-C(O)(CH_2)_p-$ or a chain of the formula $-C(O)O(CH_2)_p-$, wherein p is an integer of from 3 to 5, or one of $R^{16}$ and $R^{17}$ together with any one of $R^9$, $R^{11}$ and $R^{12}$ may form a methylene chain having the formula $-(CH_2)_p-$, wherein p is an integer from 3 to 5; and $R^{18}$ is preferably independently selected from an optionally substituted $(C_1\text{-}C_{10})$alkyl group, an optionally substituted $(C_3\text{-}C_{10})$cycloalkyl group, an optionally substituted $(C_6\text{-}C_{10})$aryl group, an optionally substituted $(C_4\text{-}C_9)$heteroaryl group, an optionally substituted $(C_7\text{-}C_{14})$aralkyl group and an optionally substituted $(C_7\text{-}C_{14})$alkaryl group.

In preferred embodiments, the electrophile may have the formula (67):

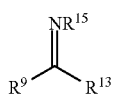

(67)

wherein $R^9$, $R^{13}$ and $R^{15}$ are as described above.

More preferably, the electrophile has the formula (68):

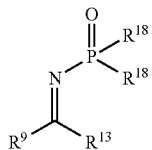

(68)

wherein $R^9$, $R^{13}$ and $R^{18}$ are as defined above.

In further preferred embodiments, the electrophile has the formula (69) or (70):

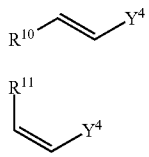

(69)

(70)

$R^{10}$, $R^{11}$ and $Y^4$ wherein R are as defined above.

In further embodiments, the reaction may be an addition reaction of a pro-nucleophile as defined above (preferably a carbon nucleophile) to an electrophile comprising a heteroatom-heteroatom double bond, such as a diimide. For example a diimide electrophile may have the formula $R^9-N=N-R^9$, wherein each $R^9$ is independently as defined above.

The "nitro-Mannich" reaction of nitroalkanes with ketimines provides an efficient route to chiral vicinal diamines and α-amino acids through carbon-carbon bond formation. However, due to the low reactivity of ketimine electrophiles and difficulties in obtaining enantiofacial discrimination towards nucleophilic addition, successful reaction protocols for the metal-free asymmetric nitro-Mannich reaction have previously been elusive. However, it has now surprisingly been found that the process of the present invention allows the desired addition products to be obtained with excellent reactivity. It is expected that the increased reactivity observed in this reaction can be attributed to the increased basicity of the iminophosphorane moiety on the bifunctional organocatalyst. Where the bifunctional organocatalyst is chiral, it has surprisingly been found that reaction products may also be obtained with high levels of enantioselectivity. This demonstrates the role of the hydrogen bond donor group in organising the electrophilic substrate so as to provide a high degree of enantiofacial discrimination by the nucleophile.

In preferred embodiments, the bifunctional organocatalyst may be generated in situ by the reaction of an azide precursor with a phosphine of the formula $P(R^1)_3$ as described below.

The compounds of the present invention may readily be prepared from azide precursors. Thus in another aspect, the present invention provides precursor compounds having the formula (71):

$$N_3-Z-NH\text{-}EWG \qquad (71)$$

wherein Z and EWG are as defined above. The precursor compounds of formula (71) may react with phosphines of the formula $(R^1)_3P$ under mild conditions to provide the compounds of formula (1) as defined above.

For the avoidance of doubt, any preferred definitions of the catalysts of formula (1) as described above, are also preferred for the corresponding azide precursors of formula (71) and the phosphines of formula $(R^1)_3P$.

In a preferred embodiment, the linking group Z contains one or more stereocentres and the compound of formula (71) is provided as a single stereoisomer.

Preferably, EWG is selected from $-C(=O)NHR^2$, and $-C(=S)NHR^2$, wherein $R^2$ is as defined above.

In some embodiments, the precursor compound has the formula (72):

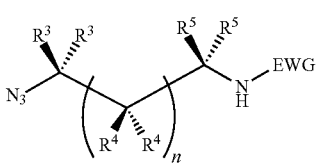

(72)

wherein $R^3$, $R^4$, $R^5$, n and EWG are as defined above.

More preferably, the precursor compound has the formula (73):

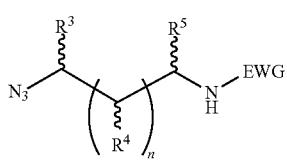
(73)

wherein $R^3$, $R^4$, $R^5$, n and EWG are as defined above.

More preferably, the precursor compound has the formula (74):

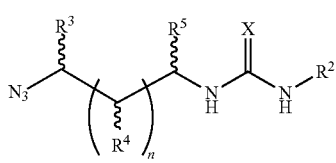
(74)

wherein $R^2$, $R^3$, each $R^4$, $R^5$, n, X and EWG are as defined above.

In further preferred embodiments, the precursor compound has the formula (75) or (76):

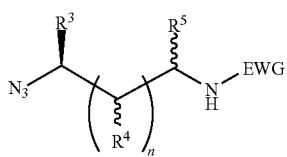
(75)

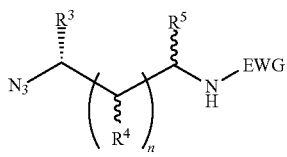
(76)

wherein: $R^3$, each $R^4$, $R^5$, EWG and n are as defined above, with the proviso that $R^3$ is not hydrogen;

or the precursor compound has the formula (77) or (78):

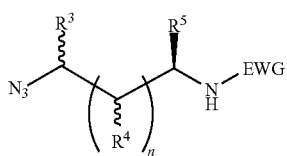
(77)

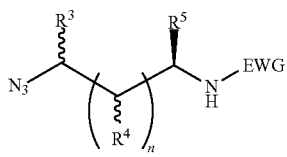
(78)

wherein: $R^3$, each $R^4$, $R^5$, EWG and n are as defined above, with the proviso that $R^5$ is not hydrogen.

In more preferred embodiments, the precursor compound has the formula (79) or (80):

(79)

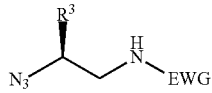
(80)

wherein: $R^3$, and EWG are as defined above, with the proviso that $R^3$ is not hydrogen;

or the precursor compound has the formula (81) or (82):

(81)

(82)

wherein: $R^5$ and EWG are as defined above, with the proviso that $R^5$ is not hydrogen;

or the precursor compound has the formula (83), (84), (85) or (86):

(83)

(84)

(85)

(86)

wherein: $R^3$, $R^5$ and EWG are as defined above, with the proviso that $R^3$ is not hydrogen and $R^5$ is not hydrogen.

In still more preferred embodiments, the precursor compound has the formula (87) or (88):

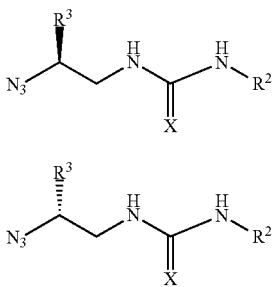

(87)

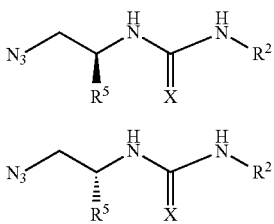

(88)

wherein: R², R³ and X are as defined above, with the proviso that R³ is not hydrogen;
or the compound of the invention has the formula (89) or (90):

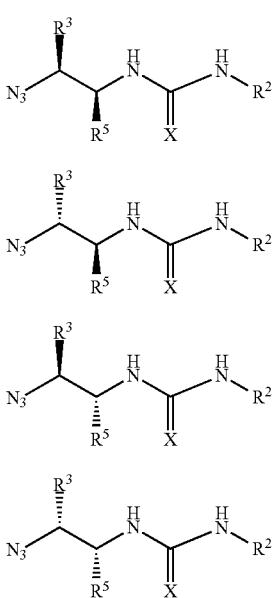

(89)

(90)

wherein: R², R⁵ and X are as defined above, with the proviso that R⁵ is not hydrogen;
or the compound of the invention has the formula (91), (92), (93) or (94):

(91)

(92)

(93)

(94)

wherein: R², R³, R⁵ and X are as defined above, with the provisos that R³ is not hydrogen and R⁵ is not hydrogen.

In another aspect, the present invention provides a process for preparing a compound having the formula (1):

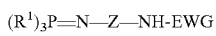

(1)

wherein $R^1$, Z and EWG are as defined above, said process comprising reacting a precursor compound as defined above with a phosphine having the formula $(R^1)_3P$, wherein $R^1$ is as defined above. Again for the avoidance of doubt, any preferred definitions of the compounds of formula (1) described above are also preferred in accordance with this aspect of the invention.

This "click"-type reaction provides compounds of formula (1) under mild conditions, in virtually quantitative yields, and without noticeable formation of any by-products other than the dinitrogen that is eliminated. This facilitates the formation of the bifunctional catalysts in situ from the catalytically inactive precursors defined above and the range of phosphines having the formula $(R^1)_3P$. In this way, the present invention avoids the need for isolation and purification of the catalytic species. However, as demonstrated in the following examples, the catalysts of the invention are stable and may be isolated and purified as required.

Preferably, the reaction is carried out in the presence of an organic solvent, preferably an aprotic organic solvent. Suitable solvents include diethyl ether, tetrahydrofuran, cyclohexane and toluene. The reaction is generally carried out at a temperature ranging from 0° C. to 50° C. and preferably at room temperature.

In a further aspect, the present invention provides the use of a catalyst of formula (1) in a reaction between a pro-nucleophile and an electrophile. Preferred definitions of the catalyst of formula (1) described above, as well as the preferred definitions of pro-nucleophiles and electrophiles described above, are also preferred in accordance with this aspect of the invention.

EXAMPLES

Example 1

Preparation of Carbamate Precursors

General procedures for the preparation of carbamate precursors of the catalysts of the invention are illustrated by reference to the preparation of precursor (101).

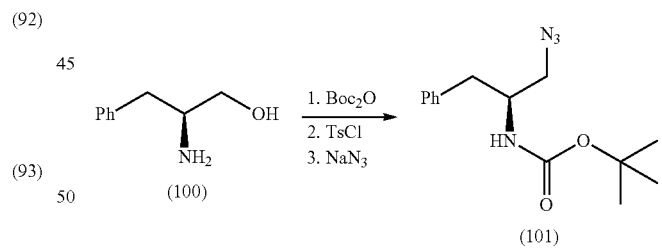

A stirred solution of aminoalcohol (100) (8.98 g, 59.5 mmol) in CH₂Cl₂ (200 mL) was cooled to 0° C. and NEt₃ (9.0 mL, 65.4 mmol) and Boc₂O (12.9 g, 59.5 mmol) were added successively. The reaction mixture was left stirring at it for 16 h, then solvents were evaporated and the resulting crude product was purified by flash column chromatography to provide 12.4 g (80%) of the N-Boc-protected aminoalcohol as a colourless solid.

A solution of N-Boc-protected aminoalcohol (12.4 g, 49.4 mmol) in CH₂Cl₂ (100 mL) was cooled to 0° C. and NEt₃ (13.7 mL, 98.8 mmol) and TsCl (9.4 g, 49.4 mmol) were added successively. The reaction mixture was left stirring at it for 24 h and then 250 mL H₂O were added. The phases were separated and the aqueous one was extracted with CH$_2$Cl$_2$. The combined organics were dried over Na$_2$SO$_4$, filtered and concentrated. The resulting crude product was purified by flash column chromatography to provide 12.0 g (60%) of the tosylate as a colourless solid.

The tosylate compound (1.25 g, 3.08 mmol) was dissolved in DMF (10 mL). NaN$_3$ (220 mg, 3.39 mmol) was added and the resulting suspension was stirred at 45° C. for 7 h. After cooling to rt, 15 mL H$_2$O were added and it was extracted with Et$_2$O, dried over Na$_2$SO$_4$, filtered and concentrated. The resulting crude product was purified by flash column chromatography to obtain 460 mg (54%) of precursor (101) as a colourless solid.

Precursor (101) may be used to prepare a carbamate catalyst according to the present invention. Alternatively, the carbamate protecting group may be removed and converted to a different hydrogen bond donor group.

It will be understood by the skilled person, that alternative routine procedures are available to produce azide precursors such as (101). For instance, the hydroxy group may be converted to an iodide leaving group instead of a sulfonate. Alternatively, the azide may be produced from a primary amine group by the use of a suitable diazo-transfer reagent.

Example 2

Preparation of Urea and Thiourea Precursors

General procedures for the preparation of urea and thiourea precursors of the catalysts of the invention are illustrated by reference to the preparation of precursor (102) from the carbamate precursor (101).

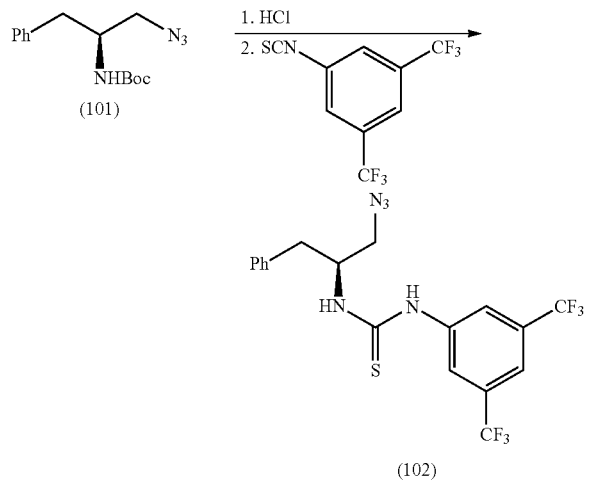

A 2M solution of HCl in Et$_2$O (15 mL, 30 mmol) was added dropwise to protected aminoazide (101) (0.386 g, 1.40 mmol) and the resulting solution was stirred at rt for 24 h. NaOH solution (2M) was added until pH 12 and the aqueous phase was extracted with Et$_2$O (3×20 mL), dried over Na$_2$SO$_4$ and concentrated. The crude aminoazide was dissolved in 5.0 mL THF, 3,5-Bis(trifluoromethyl)phenyl isothiocyanate (0.250 mL, 1.49 mmol) was added dropwise and the solution was stirred at rt for 16 h. After evaporation of the solvents, the crude product was purified by flash column chromatography to obtain 447 mg of precursor (102) (71% yield over 2 steps) as a colourless solid.

Corresponding urea precursors may be obtained by a similar procedure in which the isothiocyanate reagent is replaced by the corresponding isocyanate.

Example 3

Preparation of Amide Precursors

General procedures for the preparation of amide precursors of the catalysts of the invention are illustrated by reference to the preparation of precursor (104) from the carbamate precursor (103).

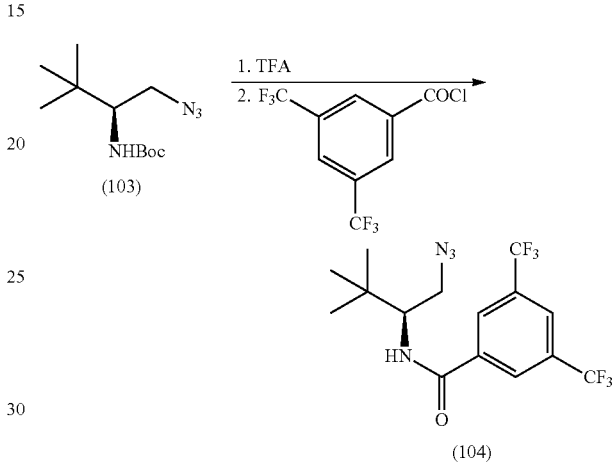

TFA (0.50 mL) was added dropwise to protected aminoazide (103) (100 mg, 0.41 mmol) at 0° C. and the resulting solution was allowed to warm to it and stirred for 3 h. NaOH solution (2M) was added until pH 12 and the aqueous phase was extracted with Et$_2$O, dried over Na$_2$SO$_4$ and concentrated. The crude aminoazide was dissolved in Et$_2$O (1.4 mL) and Et$_3$N (0.07 mL, 0.474 mmol). The solution was cooled to 0° C. and 3,5-bis(trifluoromethyl)benzoyl chloride (0.083 mL, 0.454 mmol) was added. The reaction mixture was allowed to warm to room temperature and stirred for 5 h. After evaporation of the solvents, the crude product was purified by flash column chromatography to obtain 135 mg of precursor (104) (85% yield over 2 steps) as a colourless solid.

Example 4

Preparation of Sulfonamide Precursors

General procedures for the preparation of sulfonamide precursors of the catalysts of the invention are illustrated by reference to the preparation of precursor (105) from the carbamate precursor (103).

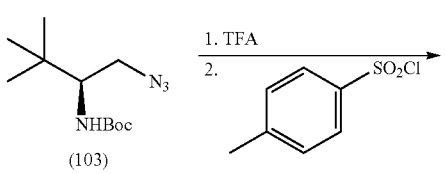

-continued

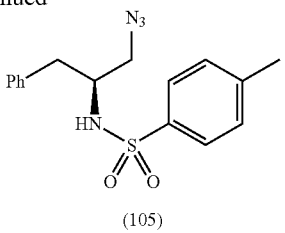

(105)

TFA (0.50 mL) was added dropwise to protected aminoazide (103) (100 mg, 0.41 mmol) at 0° C. and the resulting solution was allowed to warm to it and stirred for 3 h. NaOH solution (2M) was added until pH 12 and the aqueous phase was extracted with Et$_2$O, dried over Na$_2$SO$_4$ and concentrated. The crude aminoazide was dissolved in Et$_2$O (1.4 mL) and Et$_3$N (0.07 mL, 0.474 mmol). The solution was cooled to 0° C. and 4-toluenesulfonyl chloride (87 mg, 0.454 mmol) was added. The reaction mixture was allowed to warm to room temperature and stirred for 5 h. After evaporation of the solvents, the crude product was purified by flash column chromatography (PE-PE/EtOAc 9:1) to obtain 30 mg of precursor (105) (25% yield over 2 steps) as a colourless solid.

Example 5

Preparation of Bifunctional Catalysts

General procedures for the preparation of catalysts of the invention are illustrated by reference to the preparation of catalyst (107).

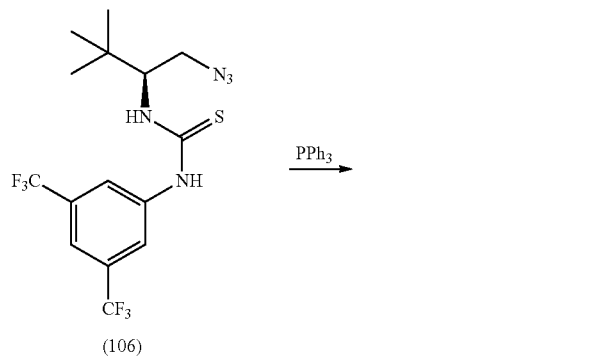

(106)

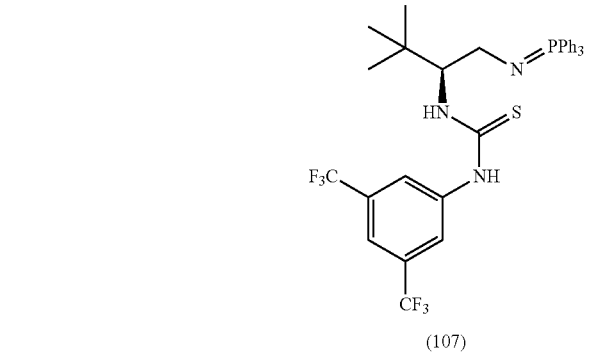

(107)

To azide (106) (300 mg, 0.726 mmol) in Et$_2$O (1.8 mL) under an argon atmosphere was added triphenylphosphine (190 mg, 0.726 mmol) at rt. Stirring was maintained at room temperature for 26 h and the reaction mixture was then concentrated in vacuo to afford a colourless foam. Pentane (4 mL) was added under N$_2$ and the mixture stirred vigorously for 2 h. The resultant suspension was filtered and dried in vacuo to afford catalyst (107) as a colourless solid (344 mg, 73% yield).

Example 6

General Procedures for the Preparation of Nitro-Mannich Addition Products

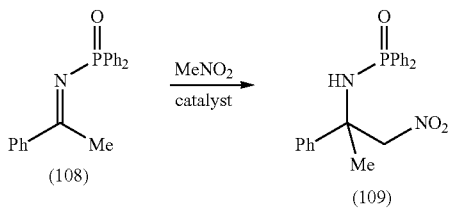

General procedure A: 0.02 mmol of catalyst is added to a stirred suspension of ketimine (108) (0.20 mmol) in MeNO$_2$ (0.22 mL, 4.0 mmol) at −15° C. and the reaction mixture stirred at −15° C. in a closed vial until disappearance of starting material by TLC or for a maximum of 96 h. The reaction is quenched by addition of 0.02 mL of 1M acetic acid solution in CH$_2$Cl$_2$ and stirred at it for 5 min. After evaporation of the solvents, $^1$H NMR conversion was measured and the crude reaction mixture was purified by flash column chromatography.

General procedure B: 0.02 mmol of catalyst is added to a stirred suspension of ketimine (108) (0.20 mmol) in MeNO$_2$ (0.22 mL, 4.0 mmol) at 0° C. and the reaction mixture stirred at 0° C. in a closed vial until disappearance of starting material by TLC or for a maximum of 48 h. The reaction is quenched by addition of 0.02 mL of 1M acetic acid solution in CH$_2$Cl$_2$ and stirred at rt for 5 min. After evaporation of the solvents, $^1$H NMR conversion was measured and the crude reaction mixture was purified by flash column chromatography.

General procedure C: 0.02 mmol of catalyst is added to a stirred suspension of ketimine (108) (0.20 mmol) in MeNO$_2$ (0.22 mL, 4.0 mmol) at rt and the reaction mixture stirred at rt in a closed vial until disappearance of starting material by TLC or for a maximum of 24 h. The reaction is quenched by addition of 0.02 mL of 1M acetic acid solution in CH$_2$Cl$_2$ and stirred at rt for 5 min. After evaporation of the solvents, $^1$H NMR conversion was measured and the crude reaction mixture was purified by flash column chromatography.

Example 7

Preparation of Racemic Nitro-Mannich Addition Products

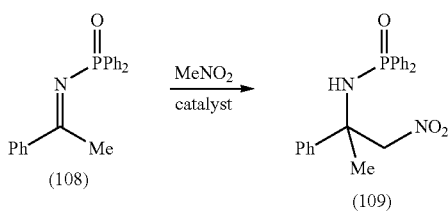

Racemic catalysts having the formula (110)-(114) were used to produce racemic nitro-Mannich addition product (109) from ketimine (108) and nitromethane using general procedure C. The results are shown in Table 1.

(110)-(114)

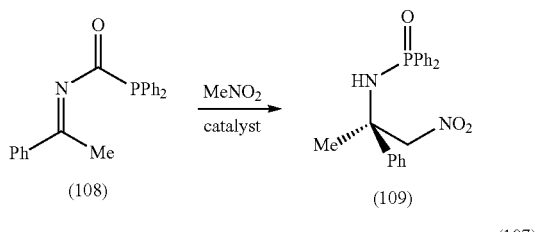
(107)

TABLE 1

| | EWG | Conversion (%) |
|---|---|---|
| 110 | *N*-(3,5-bis(trifluoromethyl)phenyl)thioamide | 98 |
| 111 | *N*-(3,5-bis(trifluoromethyl)phenyl)amide | 97 |
| 112 | 3,5-bis(trifluoromethyl)phenyl ketone | 98 |
| 113 | tosyl sulfonyl | 92 |
| 114 | tert-butyl carbamate | 99 |

Example 8

Stereoselective Preparation of Nitro-Mannich Addition Products

Effect of Linking Moiety

Catalysts having the formula (107) and (115)-(122) were used to produce nitro-Mannich addition product (109) from ketimine (108) and nitromethane using general procedure C. The results are shown in Table 2.

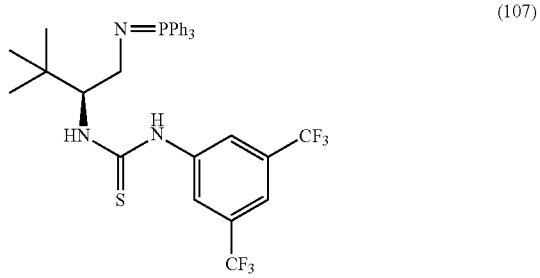
(115)

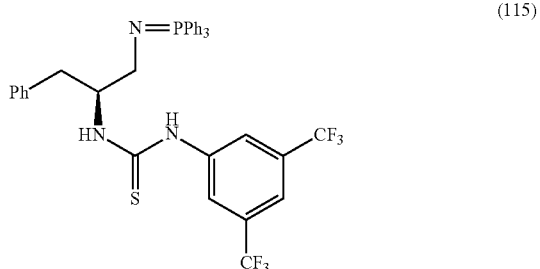
(116)

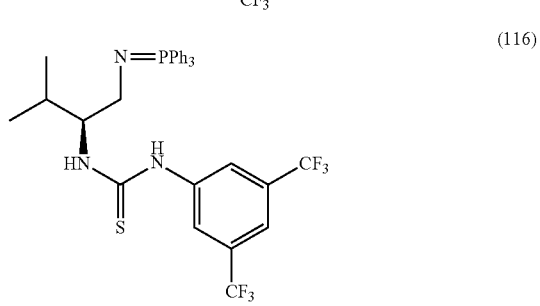
(117)

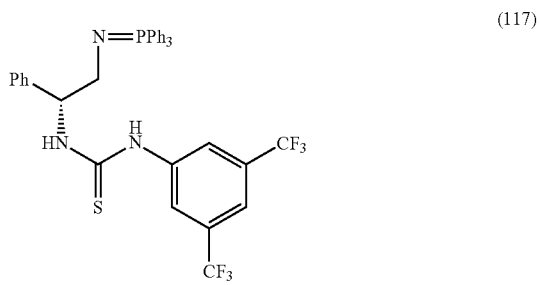
(118)

-continued

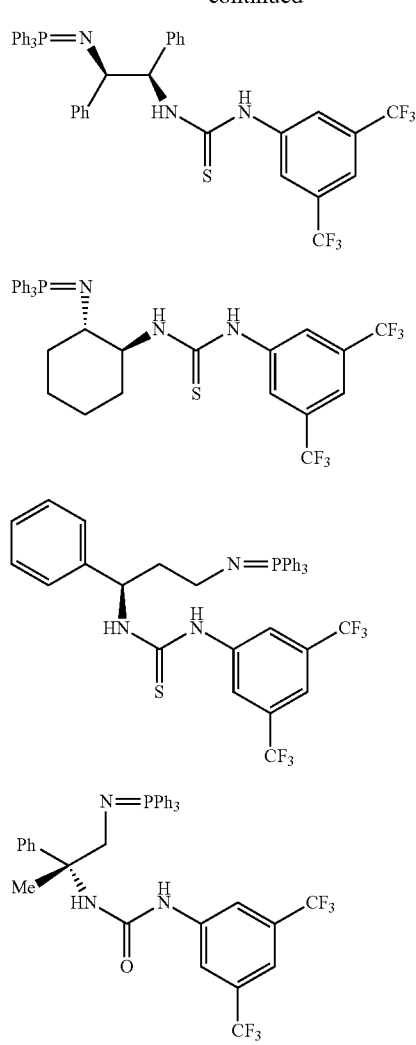

(119)
(120)
(121)
(122)

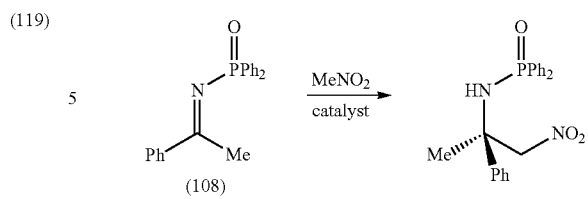

(108) → (109)

(107) and (123)-(131)

(132)-(133)

TABLE 2

| Catalyst | Conversion (%) | e.e. (%) |
|---|---|---|
| 107 | 98 | 85 |
| 115 | 93 | 78 |
| 116 | 94 | 77 |
| 117 | 95 | 77* |
| 118 | 93 | 70* |
| 119 | 48 | 34* |
| 120 | 98 | 20* |
| 121 | 98 | 7 |
| 122 | 99 | 3 |

*products obtained with opposite stereochemistry to that shown above

Example 9

Stereoselective Preparation of Nitro-Mannich Addition Products

Effect of Hydrogen Bond Donor

Catalysts having the formula (107) and (123)-(133) were used to produce nitro-Mannich addition product (109) from ketimine (108) and nitromethane using general procedure C. The results are shown in Table 3.

TABLE 3

| | EWG | Conv. (%) | e.e. (%) |
|---|---|---|---|
| 107 | (thioamide with 3,5-bis-CF₃-phenyl) | 98 | 85 |
| 123 | (thioamide with 4-methylphenyl) | 99 | 68 |
| 124 | (amide with 3,5-bis-CF₃-phenyl) | 97 | 79 |
| 125 | (thioamide with phenyl) | 98 | 73 |
| 126 | (thioamide with 4-CF₃-phenyl) | 98 | 79 |
| 127 | (ketone with 3,5-bis-CF₃-phenyl) | 98 | 11 |

TABLE 3-continued

| | EWG | Conv. (%) | e.e. (%) |
|---|---|---|---|
| 128 | ![structure with thioamide-NH-C6H4-NO2] | 98 | 86 |
| 129 | ![structure with sulfonyl-C6H4-Me] | 92 | 0 |
| 130 | ![structure with thioamide-NH-C6H4-OMe] | 98 | 70 |
| 131 | ![structure with ester-O-tBu] | 99 | 0 |
| 132 | ![structure with thioamide-NH-cyclohexyl] | 98 | 38 |
| 133 | ![structure with thioamide-NH-C(Me)2-CH2-tBu] | 98 | 38 |

The results in Table 2 demonstrate that good levels of stereoselectivity are obtained using catalysts in which the hydrogen bond donor is a thiourea or urea group. The presence of electron withdrawing groups on the thiourea or urea group increases the stereoselectivity. Lower levels of stereoselectivity are obtained with the amide catalyst (127). The sulfonamide catalyst (129) and the carbamate catalyst (131) provide negligible stereoselectivity.

Almost quantitative conversions are obtained for all systems. Systems in which the hydrogen bond donor group is an amide, sulfonamide or a carbamate thus have utility for the efficient production of achiral and racemic addition products.

Example 10

Preparation of Nitro-Mannich Addition Products

Effect of the Iminophosphorane

The effect of the iminophosphorane substituents on the reaction rate was examined by reacting ketimine (108) with nitromethane at room temperature in the presence of catalysts (107), (134) and (135) and deuterated tetrahydrofuran. The conversion to addition product (109) was measured by $^1$H NMR spectroscopy at 10 minute intervals and the results are shown in Figure 1. It is found that the reaction rate varies strongly with the substituents of the iminophosphorane moiety. The reaction with catalyst (135) is noticeably slower than with (107) or (134) which is believed to be due to the lower basicity of the iminophosphorane moiety.

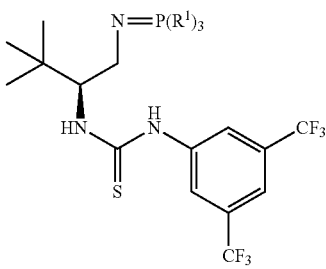

(107)-$R^1$ = Ph
(134)-$R^1$ = 4-MeOC$_6$H$_4$
(135)-$R^1$ = 4-ClC$_6$H$_4$

The reaction of ketimine (108) with nitromethane was also examined in the presence of catalyst (136), which contains an iminophosphorane derived from a tri-alkyl phosphine.

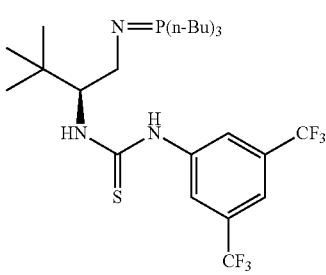

(136)

The addition product (109) was obtained after 24 h in 99% conversion and 42% e.e.

Comparative Example 11

Preparation of Nitro-Mannich Addition Products with Cinchonine-Derived Organocatalyst Example 10 was repeated using the cinchonine-derived thiourea catalyst III instead of the catalysts of the present invention. After 24 h only traces (0.04%) of the addition product were observed. This clearly demonstrates that the increased reactivity of the catalyst systems of the present invention is due to the basicity of the iminophosphorane group. Furthermore, the basicity of the catalysts according to the present invention can be tuned to the acidity of a given substrate, whereas the basicity of cinchonine derivatives cannot readily be modified.

Example 12

Stereoselective Preparation of Nitro-Mannich Addition Products

The catalyst of formula (107) was used to produce nitro-Mannich addition products from a range of ketimines and nitromethane using general procedures A and B. The results are shown in Table 2.

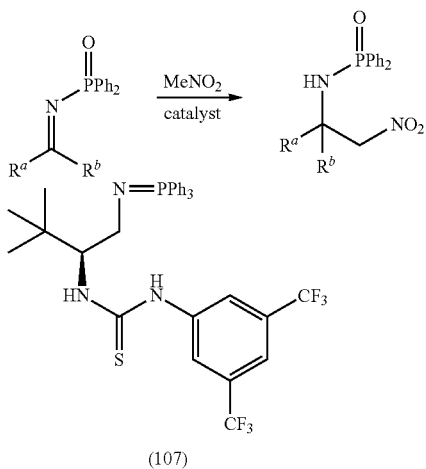

(107)

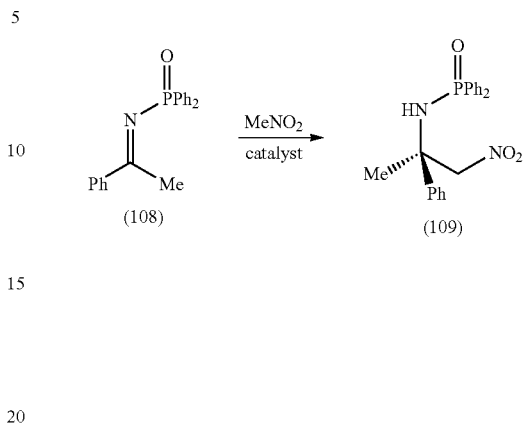

(108) (109)

TABLE 3

| $R^a$ | $R^b$ | T (° C.) | t (h) | Conversion (%) | e.e. (%) |
|---|---|---|---|---|---|
| $C_6H_5$— | Me | −15 | 96 | 89 | 95 |
| 4-MeC$_6$H$_4$— | Me | 0 | 48 | 96 | 89 |
| 4-MeOC$_6$H$_4$— | Me | 0 | 48 | 99 | 91 |
| 3-MeOC$_6$H$_4$— | Me | 0 | 48 | 98 | 91 |
| 2-MeOC$_6$H$_4$— | Me | 0 | 48 | 99 | 91 |
| 4-PhC$_6$H$_4$— | Me | 0 | 24 | 99 | 90 |
| 4-NO$_2$C$_6$H$_4$— | Me | −15 | 21 | 98 | 93 |
| 2-FC$_6$H$_4$— | Me | −15 | 96 | 90 | 94 |
| 4-FC$_6$H$_4$— | Me | 0 | 48 | 98 | 85 |
| 4-ClC$_6$H$_4$— | Me | 0 | 20 | 99 | 90 |
| 4-BrC$_6$H$_4$— | Me | −15 | 96 | 87 | 86 |
| 3,4-Cl$_2$C$_6$H$_3$— | Me | 0 | 20 | 99 | 84 |
| 3,5-(CF$_3$)$_2$C$_6$H$_3$— | Me | −15 | 96 | 99 | 90 |
| $C_6H_5$— | Et | 0 | 24 | 91 | 92 |
| 2-furyl | Me | 0 | 48 | 99 | 84 |
| 2-thienyl | Me | −15 | 96 | 17 | 92 |
| 2-thienyl | Me | 0 | 48 | 60 | 73 |
| 3-pyridyl | Me | −15 | 96 | 62 | 81 |
| 3-pyridyl | Me | 0 | 48 | 99 | 78 |
| 1-cyclohexyl | Me | −15 | 96 | 60 | 83 |
| 1-cyclohexyl | 0 | 0 | 48 | 94 | 78 |

Using the ketimine (137) at −15° C., 50% conversion and 92% e.e. was obtained after 96 h.

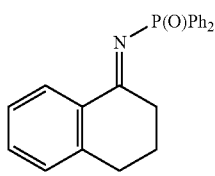

(137)

Example 13

Stereoselective Preparation of Nitro-Mannich Addition Products

Preparative Scale Reactions

The catalyst of formula (134) was used to produce nitro-Mannich addition product (109) from ketimine (108) and nitromethane using general procedure C, except that 31 mmol of ketimine (108) and 10 equiv. of MeNO$_2$ were used with only 1 mol % of catalyst. The nitro-Mannich addition product (109) was obtained after 21 h in 70% yield and 98% ee after recrystallisation.

Example 14

Stereoselective Preparation of Michael Addition Products

The Michael addition reaction of compound (138) to nitrostyrene (139) was examined in the presence of 10 mol % of catalyst (134).

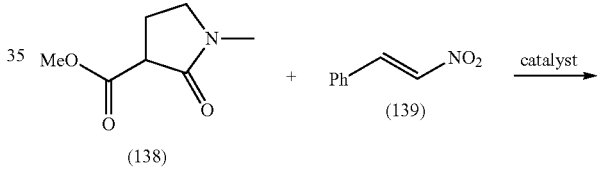

(138) (139)

(140)

The reaction product (140) was obtained in 95% yield after 12 h at −40° C., with an e.e. of 91% and a diastereomeric ratio (d.r.) of 8.3:1. This reaction has previously been reported in the presence of 20 mol % of cinchonine-derived catalyst Ill. At −20° C., the reaction catalysed by Ill takes 14 days to completion, and reaction products are obtained with lower e.e. (90%) and lower d.r. (2:1). Using catalyst (134) under the same conditions (−20° C.), the reaction product is obtained in 15 minutes with 97% yield, 84% e.e., and a d.r. 6:1.

Example 15
Further Examples of Catalysts
The following compounds were also prepared, and were shown to be effective as stereoselective catalysts:
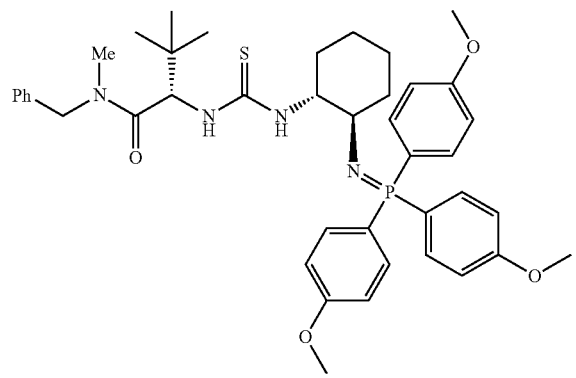
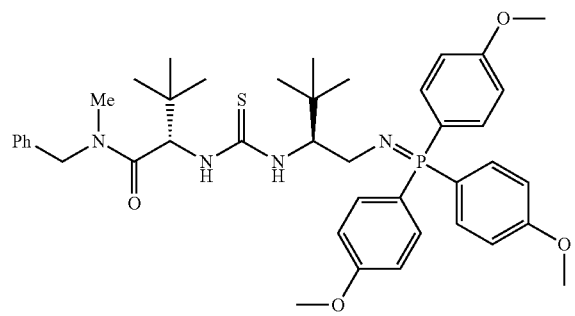
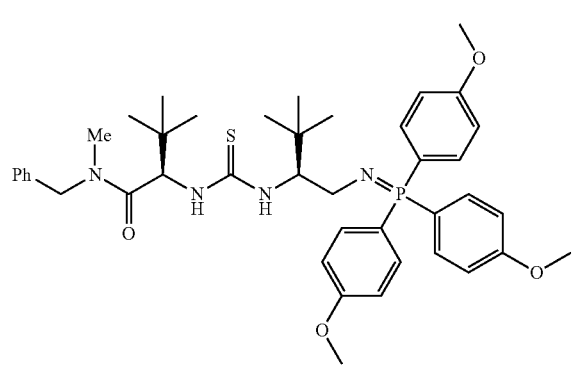
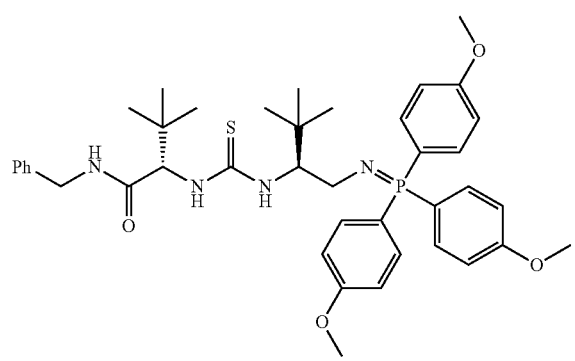
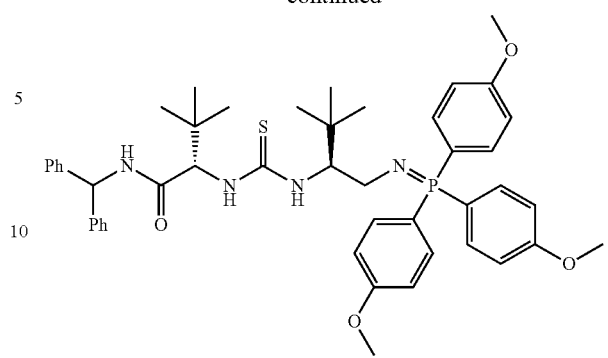
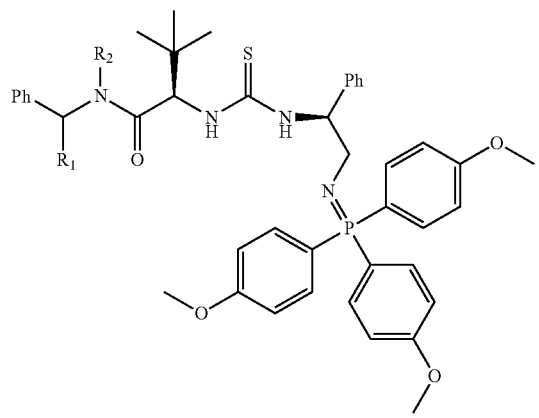
where:
$R^1=R^2=H$;
$R^1=H, R^2=Me$;
$R^1=Ph, R^2=H$,
$R^1=Ph, R^2=Me$; or
$R^1=Ph, R^2=H$,
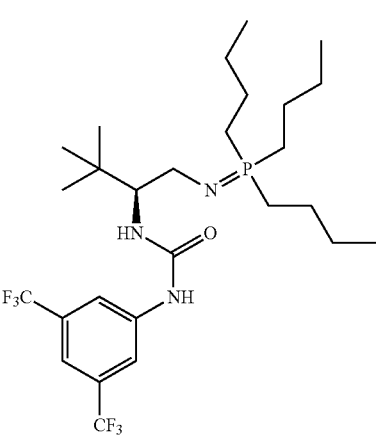

67
-continued
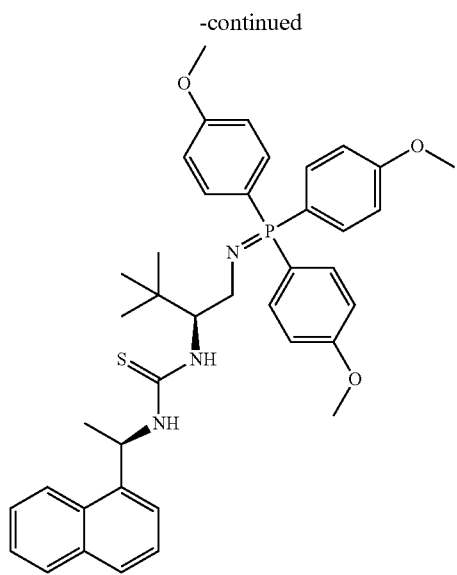
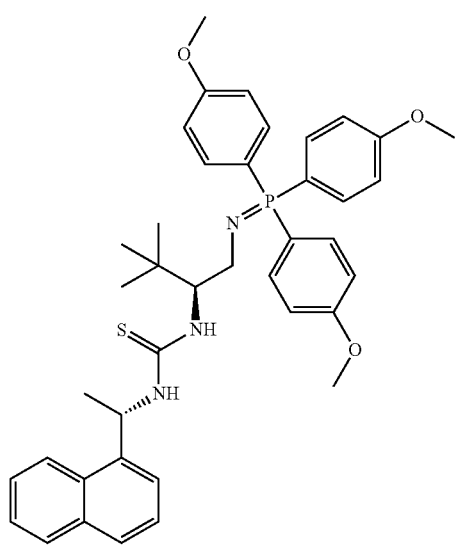
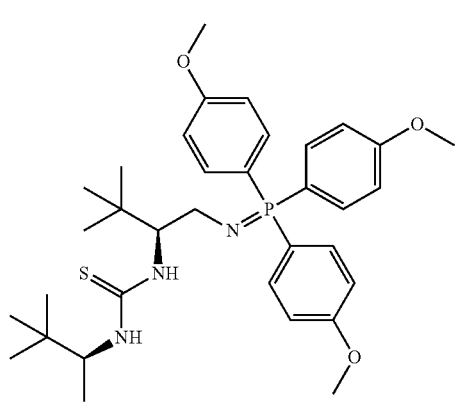
68
-continued
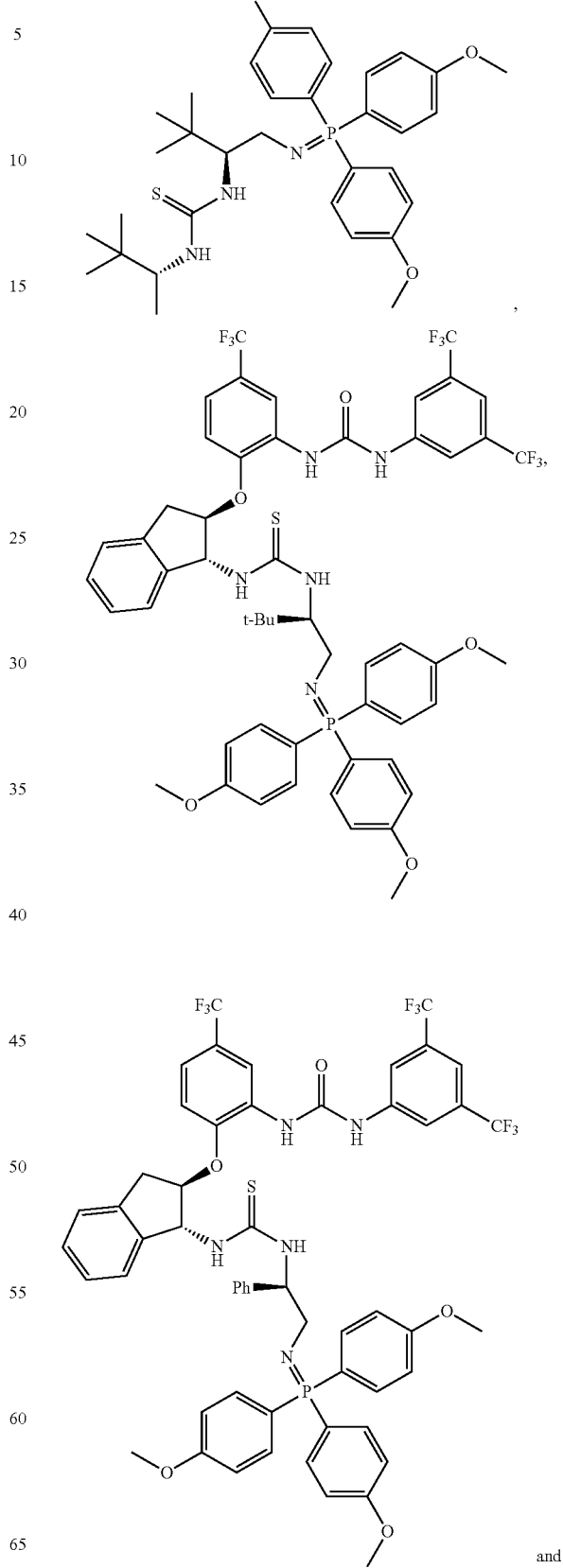
and -continued

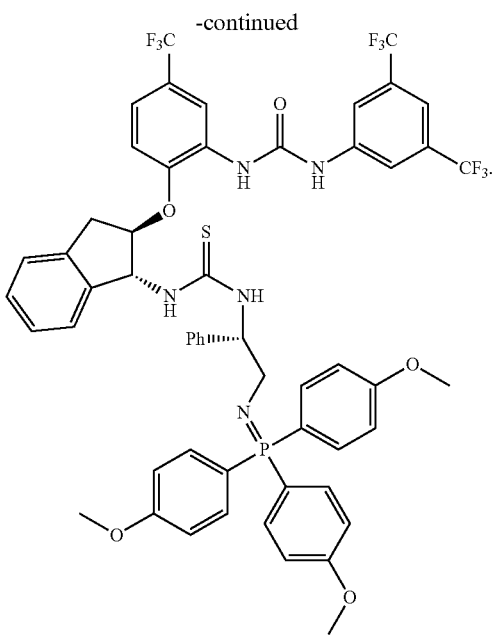

The invention claimed is:
1. A catalyst having the formula (2):

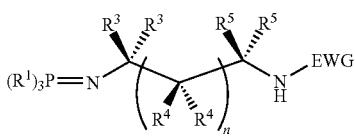

(2)

wherein:
each $R^1$ is independently selected from the group consisting of an optionally substituted alkyl group, an optionally substituted cycloalkyl group, an optionally substituted aryl group, an optionally substituted heteroaryl group, an optionally substituted aralkyl group and an optionally substituted alkaryl group;
EWG is an electron-withdrawing group selected from the group consisting of groups having the formulae $-C(=X)NHR^2$, $-C(=X)R^2$, $-SO_2R^2$ and $-C(=X)XR^2$, wherein X is selected from the group consisting of O and S, and wherein $R^2$ is selected from the group consisting of an optionally substituted alkyl group, an optionally substituted cycloalkyl group, an optionally substituted aryl group, an optionally substituted heteroaryl group, an optionally substituted aralkyl group and an optionally substituted alkaryl group;
$R^3$, $R^4$ and $R^5$ are independently selected from the group consisting of hydrogen, an optionally substituted ($C_1$-$C_{10}$)alkyl group, an optionally substituted ($C_3$-$C_{10}$)cycloalkyl group, an optionally substituted ($C_6$-$C_{10}$)aryl group, an optionally substituted ($C_4$-$C_9$)heteroaryl group, an optionally substituted ($C_7$-$C_{14}$)aralkyl group, an optionally substituted ($C_{13}$-$C_{20}$)di-aryl-alkyl group and an optionally substituted ($C_7$-$C_{14}$)alkaryl group, or any two of $R^3$, $R^4$ or $R^5$ on adjacent carbon atoms may together form a methylene chain having the formula $-(CH_2)_m-$, wherein m is an integer of from 3 to 5, and wherein at least one of $R^3$, $R^4$ and $R^5$ is not hydrogen; and
n is an integer of from 0 to 3.

2. A catalyst according to claim 1, wherein each $R^1$ is independently selected from the group consisting of an optionally substituted ($C_1$-$C_{10}$)alkyl group, an optionally substituted ($C_3$-$C_{10}$)cycloalkyl group, an optionally substituted ($C_6$-$C_{10}$)aryl group, an optionally substituted ($C_4$-$C_9$)heteroaryl group, an optionally substituted ($C_7$-$C_{14}$)aralkyl group and an optionally substituted ($C_7$-$C_{14}$)alkaryl group.

3. A catalyst according to claim 1, wherein EWG is selected from the group consisting of $-C(=O)NHR^2$ and $-C(=S)NHR^2$, wherein $R^2$ is selected from the group consisting of an optionally substituted alkyl group, an optionally substituted cycloalkyl group, an optionally substituted aryl group, an optionally substituted heteroaryl group, an optionally substituted aralkyl group and an optionally substituted alkaryl group; or EWG is selected from the group consisting of $-C(=O)NHR^2$ and $-C(=S)NHR^2$, wherein $R^2$ is selected from the group consisting of an optionally substituted ($C_1$-$C_{10}$)alkyl group, an optionally substituted ($C_3$-$C_{10}$)cycloalkyl group, an optionally substituted ($C_6$-$C_{10}$)aryl group, an optionally substituted ($C_4$-$C_9$)heteroaryl group, an optionally substituted ($C_7$-$C_{14}$)aralkyl group and an optionally substituted ($C_7$-$C_{14}$)alkaryl group.

4. A catalyst according to claim 1, wherein EWG has the formula:

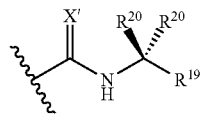

wherein:
X' is selected from the group consisting of S and O;
$R^{19}$ is selected from the group consisting of hydrogen and $-C(=Z')N(R^{21})_2$, wherein Z' is selected from the group consisting of S and O, and each $R^{21}$ is independently selected from the group consisting of hydrogen, an optionally substituted ($C_1$-$C_{10}$)alkyl group, an optionally substituted ($C_3$-$C_{10}$)cycloalkyl group, an optionally substituted ($C_6$-$C_{10}$)aryl group, an optionally substituted ($C_4$-$C_9$)heteroaryl group, an optionally substituted ($C_7$-$C_{14}$)aralkyl group and an optionally substituted ($C_7$-$C_{14}$)alkaryl group; and
each $R^{20}$ is independently selected from the group consisting of hydrogen, an optionally substituted ($C_1$-$C_{10}$) alkyl group, an optionally substituted ($C_3$-$C_{10}$)cycloalkyl group, an optionally substituted ($C_6$-$C_{10}$)aryl group, an optionally substituted ($C_4$-$C_9$)heteroaryl group, an optionally substituted ($C_7$-$C_{14}$)aralkyl group and an optionally substituted ($C_7$-$C_{14}$)alkaryl group; or
EWG is:

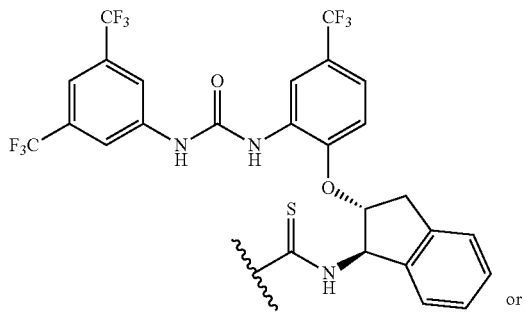

or

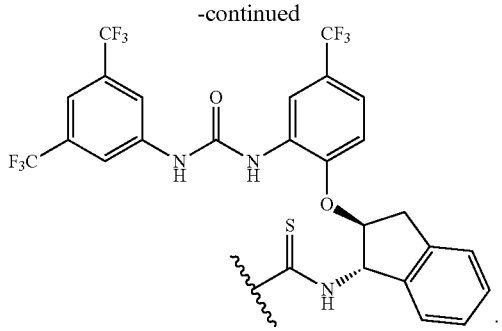

5. A catalyst according to claim 1, having the formula (3):

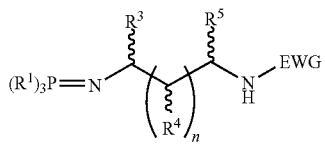
(3)

or having the formula (4);

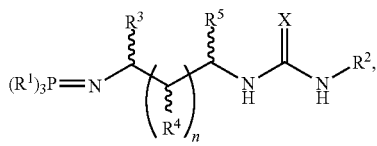
(4)

wherein X is S or O.

6. A catalyst according to claim 5, wherein at least one of $R^3$ and $R^5$ is selected from the group consisting of methyl, ethyl, n-propyl, iso-propyl, n-butyl, iso-butyl, sec-butyl, tert-butyl, phenyl, 4-methylphenyl, 4-methoxyphenyl, 2,5-dimethyl phenyl, benzyl, 4-methoxybenzyl, diphenylmethyl, iso-propyloxymethyl and tert-butyloxymethyl, or in the case where n is 0, $R^3$ and $R^5$ may together form a methylene chain having the formula —$(CH_2)_m$—, wherein m is 3 or 4.

7. A catalyst according to claim 1, wherein n is an integer from 0 to 2.

8. A catalyst according to claim 1, having the formula (5) or (6):

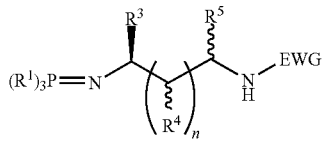
(5)

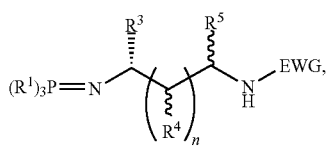
(6)

with the proviso that $R^3$ is not hydrogen;

or having the formula (7) or (8):

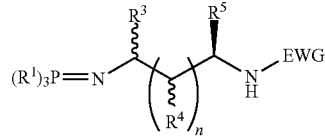
(7)

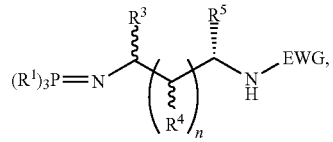
(8)

with the proviso that $R^5$ is not hydrogen; or having the formula (9) or (10):

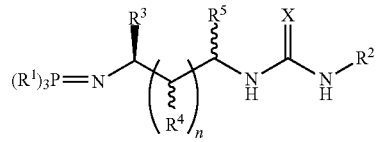
(9)

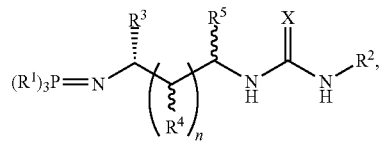
(10)

with the proviso that $R^3$ is not hydrogen;
or having the formula (11) or (12):

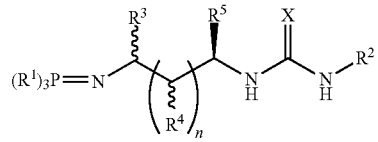
(11)

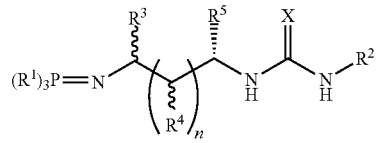
(12)

with the proviso that $R^5$ is not hydrogen;
or having the formula (13) or (14):

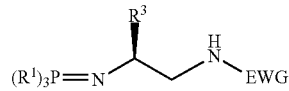
(13)

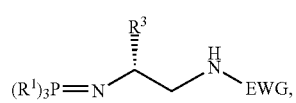
(14)

with the proviso that $R^3$ is not hydrogen;

or having formula (15) or (16):

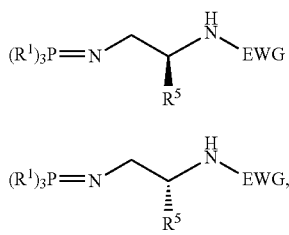

with the proviso that $R^5$ is not hydrogen;
or having the formula (17), (18), (19) or (20):

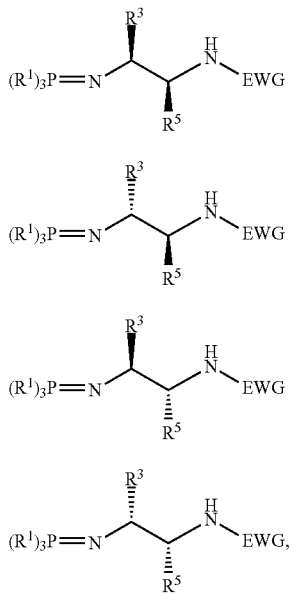

with the provisos that $R^3$ is not hydrogen and $R^5$ is not hydrogen, or having the formula (21) or (22):

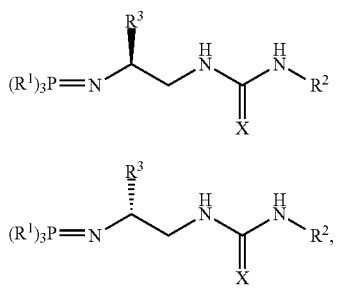

with the proviso that $R^3$ is not hydrogen;

or having the formula (23) or (24):

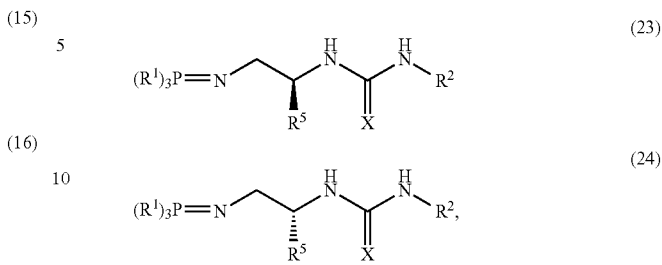

with the proviso that $R^5$ is not hydrogen;
or having the formula (25), (26), (27) or (28):

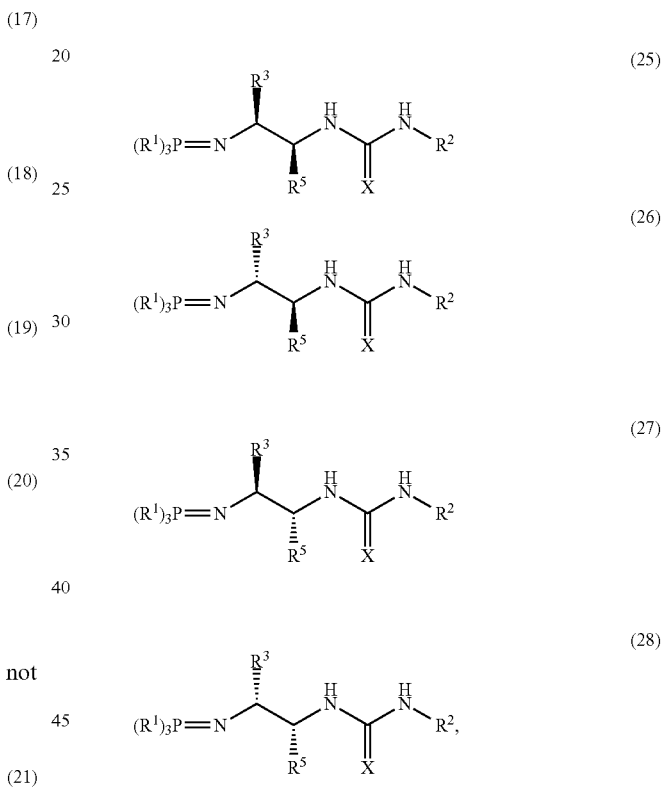

with the provisos that $R^3$ is not hydrogen and $R^5$ is not hydrogen; or having the formula (23) or (24) wherein X is S, $R^1$ is phenyl or 4-methoxyphenyl, $R^2$ is selected from the group consisting of 4-(trifluoromethylphenyl), 3,5-bis-(trifluoromethyl)phenyl and 4-nitrophenyl, and $R^5$ is selected from the group consisting of iso-propyl, tert-butyl, phenyl, benzyl and diphenylmethyl.

9. A catalyst according to claim 7, wherein n is 0 or 1.

10. A catalyst according to claim 9, wherein n is 0.

* * * * *